(12) United States Patent
Crozet et al.

(10) Patent No.: US 8,906,020 B2
(45) Date of Patent: Dec. 9, 2014

(54) DYNAMIC EXTERNAL FIXATOR AND METHODS FOR USE

(71) Applicant: Stryker Trauma SA, Selzach (CH)

(72) Inventors: Yves Stephane Crozet, Ramsey, NJ (US); Gurvinderjit Singh Wakia, New Delhi (IN); Manoj Kumar Singh, Mahwah, NJ (US)

(73) Assignee: Stryker Trauma SA (CH)

( * ) Notice: Subject to any disclaimer, the term of this patent is extended or adjusted under 35 U.S.C. 154(b) by 29 days.

(21) Appl. No.: 13/788,466

(22) Filed: Mar. 7, 2013

(65) Prior Publication Data

US 2013/0253512 A1    Sep. 26, 2013

Related U.S. Application Data

(63) Continuation-in-part of application No. 12/573,310, filed on Oct. 5, 2009.

(51) Int. Cl.
  *A61B 17/62* (2006.01)
  *A61B 17/88* (2006.01)
  *A61B 17/64* (2006.01)

(52) U.S. Cl.
  CPC .............. *A61B 17/62* (2013.01); *A61B 17/88* (2013.01); *A61B 17/6441* (2013.01)
  USPC ......................................................... 606/54

(58) Field of Classification Search
  CPC ........................... A61B 17/62; A61B 17/6441
  USPC ..................................................... 606/54–59
  See application file for complete search history.

(56) References Cited

U.S. PATENT DOCUMENTS

| 6,214 A | 3/1849 | Yerger |
| 2,333,033 A | 10/1943 | Mraz |
| 2,391,537 A | 12/1945 | Anderson |

(Continued)

FOREIGN PATENT DOCUMENTS

| CH | 596826 A5 | 3/1978 |
| EP | 611007 A1 | 8/1994 |

(Continued)

OTHER PUBLICATIONS

Partial European Search Report for Application No. EP13180720 dated Dec. 3, 2013.

(Continued)

*Primary Examiner* — Pedro Philogene
*Assistant Examiner* — David Comstock
(74) *Attorney, Agent, or Firm* — Lerner, David, Littenberg, Krumholz & Mentlik, LLP

(57) ABSTRACT

An external fixation system has a planar ring with an adjustable device having a body releasably mounted on the ring. The adjustable device includes a first member for movement in a direction generally perpendicular to the ring. A second member is mounted on the first member for movement in a direction parallel to a side wall of the planar ring. A method for treating a broken bone includes providing an external fixation system and inserting a first k-wire or half pin through a first piece of the bone and affixing the first k-wire or half pin to the ring, then inserting a second k-wire or half pin through a second piece of bone and affixing the second k-wire or half pin to the adjustable device. The pieces of bone are realigned, compressed, or distracted by adjusting at least one of the first and second adjustable members.

22 Claims, 30 Drawing Sheets

(56) References Cited

U.S. PATENT DOCUMENTS

| | | |
|---|---|---|
| 2,393,831 A | 1/1946 | Stader |
| 3,727,610 A | 4/1973 | Riniker |
| 3,985,127 A | 10/1976 | Volkov et al. |
| 4,100,919 A | 7/1978 | Oganesyan et al. |
| 4,185,623 A | 1/1980 | Volkov et al. |
| 4,338,927 A | 7/1982 | Volkov et al. |
| 4,548,199 A | 10/1985 | Agee |
| 5,074,866 A | 12/1991 | Sherman et al. |
| 5,087,258 A | 2/1992 | Schewior |
| 5,112,331 A | 5/1992 | Miletich |
| 5,122,140 A | 6/1992 | Asche et al. |
| 5,207,676 A | 5/1993 | Canadell et al. |
| 5,353,504 A | 10/1994 | Pai |
| 5,391,167 A | 2/1995 | Pong et al. |
| 5,437,666 A | 8/1995 | Tepic et al. |
| 5,451,225 A | 9/1995 | Ross, Jr. et al. |
| 5,540,686 A | 7/1996 | Zippel et al. |
| 5,630,814 A | 5/1997 | Ross, Jr. et al. |
| 5,658,283 A | 8/1997 | Huebner |
| 5,662,648 A | 9/1997 | Faccioli et al. |
| 5,681,309 A | 10/1997 | Ross, Jr. et al. |
| 5,688,271 A | 11/1997 | Faccioli et al. |
| 5,702,389 A | 12/1997 | Taylor et al. |
| 5,713,897 A | 2/1998 | Goble et al. |
| 5,725,526 A | 3/1998 | Allard et al. |
| 5,725,527 A | 3/1998 | Biedermann et al. |
| 5,728,095 A | 3/1998 | Taylor et al. |
| 5,766,173 A | 6/1998 | Ross, Jr. et al. |
| 5,776,132 A | 7/1998 | Blyakher |
| 5,776,173 A | 7/1998 | Madsen, Jr. et al. |
| 5,788,695 A | 8/1998 | Richardson |
| 5,797,908 A | 8/1998 | Meyers et al. |
| 5,843,081 A | 12/1998 | Richardson |
| 5,846,245 A | 12/1998 | McCarthy et al. |
| 5,863,292 A | 1/1999 | Tosic |
| 5,891,143 A | 4/1999 | Taylor et al. |
| 5,897,555 A | 4/1999 | Clyburn et al. |
| 5,919,192 A | 7/1999 | Shouts |
| 5,921,985 A | 7/1999 | Ross, Jr. et al. |
| 5,928,230 A | 7/1999 | Tosic |
| 5,931,837 A | 8/1999 | Marsh et al. |
| 5,971,984 A | 10/1999 | Taylor et al. |
| 5,976,133 A | 11/1999 | Kraus et al. |
| 6,007,535 A | 12/1999 | Rayhack et al. |
| 6,010,501 A | 1/2000 | Raskin et al. |
| 6,013,081 A | 1/2000 | Burkinshaw et al. |
| 6,030,386 A | 2/2000 | Taylor et al. |
| 6,036,691 A | 3/2000 | Richardson |
| 6,245,071 B1 | 6/2001 | Pierson |
| 6,328,737 B1 | 12/2001 | Moorcroft et al. |
| 6,342,052 B1 | 1/2002 | Allende |
| 6,342,054 B1 | 1/2002 | Mata |
| 6,423,061 B1 | 7/2002 | Bryant |
| 6,491,694 B1 | 12/2002 | Orsak |
| 6,537,275 B2 | 3/2003 | Venturini et al. |
| 6,610,063 B2 | 8/2003 | Kumar et al. |
| 6,613,049 B2 | 9/2003 | Winquist et al. |
| 6,648,891 B2 | 11/2003 | Kim |
| 6,652,524 B1 | 11/2003 | Weiner |
| 6,746,448 B2 | 6/2004 | Weiner et al. |
| 6,784,125 B1 | 8/2004 | Yamakawa et al. |
| 6,793,655 B2 | 9/2004 | Orsak |
| 6,860,883 B2 | 3/2005 | Janowski et al. |
| 6,964,663 B2 | 11/2005 | Grant et al. |
| 7,048,735 B2 | 5/2006 | Ferrante et al. |
| 7,147,640 B2 | 12/2006 | Huebner et al. |
| 7,261,713 B2 | 8/2007 | Langmaid et al. |
| 7,276,069 B2 | 10/2007 | Biedermann et al. |
| 7,291,148 B2 | 11/2007 | Agee et al. |
| 7,311,711 B2 | 12/2007 | Cole |
| 7,361,176 B2 | 4/2008 | Cooper et al. |
| 7,422,593 B2 | 9/2008 | Cresina et al. |
| 7,449,023 B2 | 11/2008 | Walulik et al. |
| 7,468,063 B2 | 12/2008 | Walulik et al. |
| 7,479,142 B2 | 1/2009 | Weiner et al. |
| 7,491,008 B2 | 2/2009 | Thomke et al. |
| 7,507,240 B2 | 3/2009 | Olsen |
| 7,527,626 B2 | 5/2009 | Lutz et al. |
| 7,575,575 B2 | 8/2009 | Olsen et al. |
| 7,578,822 B2 | 8/2009 | Rezach et al. |
| RE40,914 E | 9/2009 | Taylor et al. |
| 7,608,074 B2 | 10/2009 | Austin et al. |
| 7,632,271 B2 | 12/2009 | Baumgartner et al. |
| 7,699,848 B2 | 4/2010 | Hoffman et al. |
| 7,708,736 B2 | 5/2010 | Mullaney |
| 7,749,224 B2 | 7/2010 | Cresina et al. |
| 7,763,020 B2 | 7/2010 | Draper |
| 7,803,158 B2 | 9/2010 | Hayden |
| 7,806,843 B2 | 10/2010 | Marin |
| 7,815,586 B2 | 10/2010 | Grant et al. |
| 7,875,030 B2 | 1/2011 | Hoffmann-Clair et al. |
| 7,881,771 B2 | 2/2011 | Koo et al. |
| 7,887,498 B2 | 2/2011 | Marin |
| 7,887,537 B2 | 2/2011 | Ferrante et al. |
| 7,931,650 B2 | 4/2011 | Winquist et al. |
| 7,938,829 B2 | 5/2011 | Mullaney |
| 7,955,333 B2 | 6/2011 | Yeager |
| 7,955,334 B2 | 6/2011 | Steiner et al. |
| 7,985,221 B2 | 7/2011 | Coull et al. |
| 8,029,505 B2 | 10/2011 | Hearn et al. |
| 8,057,474 B2 | 11/2011 | Knuchel et al. |
| 8,114,077 B2 | 2/2012 | Steiner et al. |
| 8,137,347 B2 | 3/2012 | Weiner et al. |
| 8,142,432 B2 | 3/2012 | Matityahu |
| 8,147,490 B2 | 4/2012 | Bauer |
| 8,147,491 B2 | 4/2012 | Lavi |
| 8,157,800 B2 | 4/2012 | Vvedensky et al. |
| 8,172,849 B2 | 5/2012 | Noon et al. |
| 8,182,483 B2 | 5/2012 | Bagnasco et al. |
| 8,187,274 B2 | 5/2012 | Schulze |
| 8,192,434 B2 | 6/2012 | Huebner et al. |
| 8,202,273 B2 | 6/2012 | Karidis |
| 8,241,285 B2 | 8/2012 | Mullaney |
| 8,251,937 B2 | 8/2012 | Marin |
| 8,282,652 B2 | 10/2012 | Mackenzi et al. |
| 2001/0049526 A1 | 12/2001 | Venturini et al. |
| 2002/0013584 A1 | 1/2002 | Termaten |
| 2002/0042613 A1 | 4/2002 | Mata |
| 2002/0165543 A1 | 11/2002 | Winquist et al. |
| 2003/0069580 A1 | 4/2003 | Langmaid et al. |
| 2003/0106230 A1 | 6/2003 | Hennessey |
| 2003/0109879 A1 | 6/2003 | Orsak |
| 2003/0181911 A1 | 9/2003 | Venturini |
| 2003/0191466 A1 | 10/2003 | Austin et al. |
| 2003/0216734 A1 | 11/2003 | Mingozzi et al. |
| 2003/0225406 A1 | 12/2003 | Weiner et al. |
| 2004/0073211 A1 | 4/2004 | Austin et al. |
| 2004/0097944 A1 | 5/2004 | Koman et al. |
| 2004/0116926 A1 | 6/2004 | Venturini et al. |
| 2004/0133199 A1 | 7/2004 | Coati et al. |
| 2004/0133200 A1 | 7/2004 | Ruch et al. |
| 2005/0043730 A1 | 2/2005 | Janowski et al. |
| 2005/0059968 A1 | 3/2005 | Grant et al. |
| 2005/0113829 A1 | 5/2005 | Walulik et al. |
| 2005/0119656 A1 | 6/2005 | Ferrante et al. |
| 2005/0149018 A1 | 7/2005 | Cooper et al. |
| 2005/0234448 A1 | 10/2005 | McCarthy |
| 2006/0155276 A1 | 7/2006 | Walulik et al. |
| 2006/0229605 A1 | 10/2006 | Olsen |
| 2006/0235383 A1 | 10/2006 | Hollawell |
| 2006/0276786 A1 | 12/2006 | Brinker |
| 2006/0287652 A1 | 12/2006 | Lessig et al. |
| 2007/0038217 A1 | 2/2007 | Brown et al. |
| 2007/0043354 A1 | 2/2007 | Koo et al. |
| 2007/0049930 A1 | 3/2007 | Hearn et al. |
| 2007/0055233 A1 | 3/2007 | Brinker |
| 2007/0123857 A1 | 5/2007 | Deffenbaugh et al. |
| 2007/0161983 A1 | 7/2007 | Cresina et al. |
| 2007/0161984 A1 | 7/2007 | Cresina et al. |
| 2007/0225704 A1 | 9/2007 | Ziran et al. |
| 2007/0233061 A1 | 10/2007 | Lehmann et al. |
| 2007/0255280 A1 | 11/2007 | Austin et al. |
| 2007/0282338 A1 | 12/2007 | Mullaney |
| 2008/0228185 A1 | 9/2008 | Vasta et al. |

(56) References Cited

U.S. PATENT DOCUMENTS

| | | |
|---|---|---|
| 2008/0269741 A1 | 10/2008 | Karidis |
| 2009/0018541 A1 | 1/2009 | Lavi |
| 2009/0036890 A1 | 2/2009 | Karidis |
| 2009/0036891 A1 | 2/2009 | Brown et al. |
| 2009/0105621 A1 | 4/2009 | Boyd et al. |
| 2009/0131935 A1 | 5/2009 | Yeager |
| 2009/0177198 A1 | 7/2009 | Theodoros et al. |
| 2009/0198234 A1 | 8/2009 | Knuchel et al. |
| 2009/0264883 A1 | 10/2009 | Steiner et al. |
| 2009/0287212 A1 | 11/2009 | Hirata et al. |
| 2009/0312757 A1 | 12/2009 | Kehres et al. |
| 2010/0145336 A1 | 6/2010 | Draper |
| 2010/0179548 A1 | 7/2010 | Marin |
| 2010/0191239 A1 | 7/2010 | Sakkers et al. |
| 2010/0234844 A1 | 9/2010 | Edelhauser et al. |
| 2010/0249779 A1 | 9/2010 | Hotchkiss et al. |
| 2010/0280516 A1 | 11/2010 | Taylor |
| 2010/0298827 A1 | 11/2010 | Cremer et al. |
| 2010/0305568 A1 | 12/2010 | Ross et al. |
| 2010/0312243 A1 | 12/2010 | Ross et al. |
| 2010/0331840 A1 | 12/2010 | Ross et al. |
| 2011/0060336 A1 | 3/2011 | Pool et al. |
| 2011/0066151 A1 | 3/2011 | Murner et al. |
| 2011/0082458 A1 | 4/2011 | Crozet et al. |
| 2011/0098707 A1 | 4/2011 | Mullaney |
| 2011/0112533 A1 | 5/2011 | Venturini et al. |
| 2011/0118737 A1 | 5/2011 | Vasta et al. |
| 2011/0118738 A1 | 5/2011 | Vasta et al. |
| 2011/0172663 A1 | 7/2011 | Mullaney |
| 2011/0172664 A1 | 7/2011 | Bagnasco et al. |
| 2011/0245830 A1 | 10/2011 | Zgonis et al. |
| 2011/0313418 A1 | 12/2011 | Nikonovas |
| 2011/0313419 A1 | 12/2011 | Mullaney |
| 2012/0004659 A1 | 1/2012 | Miller et al. |
| 2012/0041439 A1 | 2/2012 | Singh et al. |
| 2012/0078251 A1 | 3/2012 | Benenati et al. |
| 2012/0089142 A1 | 4/2012 | Mullaney et al. |
| 2012/0095462 A1 | 4/2012 | Miller |
| 2012/0136355 A1 | 5/2012 | Wolfson |
| 2012/0143190 A1 | 6/2012 | Wolfson |

FOREIGN PATENT DOCUMENTS

| | | |
|---|---|---|
| EP | 1016381 | 12/2003 |
| EP | 2417923 A1 | 2/2012 |
| EP | 2417924 A1 | 2/2012 |
| FR | 2576774 A1 | 8/1986 |
| WO | 2007/111576 A2 | 10/2007 |
| WO | 2010104567 A1 | 9/2010 |
| WO | 2012102685 A1 | 8/2012 |

OTHER PUBLICATIONS

BIOMET® Vision™ Footing™ System: Surgical Technique, 39 pages, (2008).
Nanua et al., IEEE Transactions on Robotics and Automation, vol. 6, No. 4, pp. 438-444, Aug. 1990.
European Search Report, EP 10 172 523 dated Mar. 25, 2011.
European Search Report, EP 11176512, dated Sep. 19, 2011.
European Search Report, EP 11176566, dated Sep. 20, 2011.
U.S. Appl. No. 13/592,832, filed Aug. 23, 2013 (not yet published).
U.S. Appl. No. 13/788,466, filed Mar. 7, 2013 (not yet published).

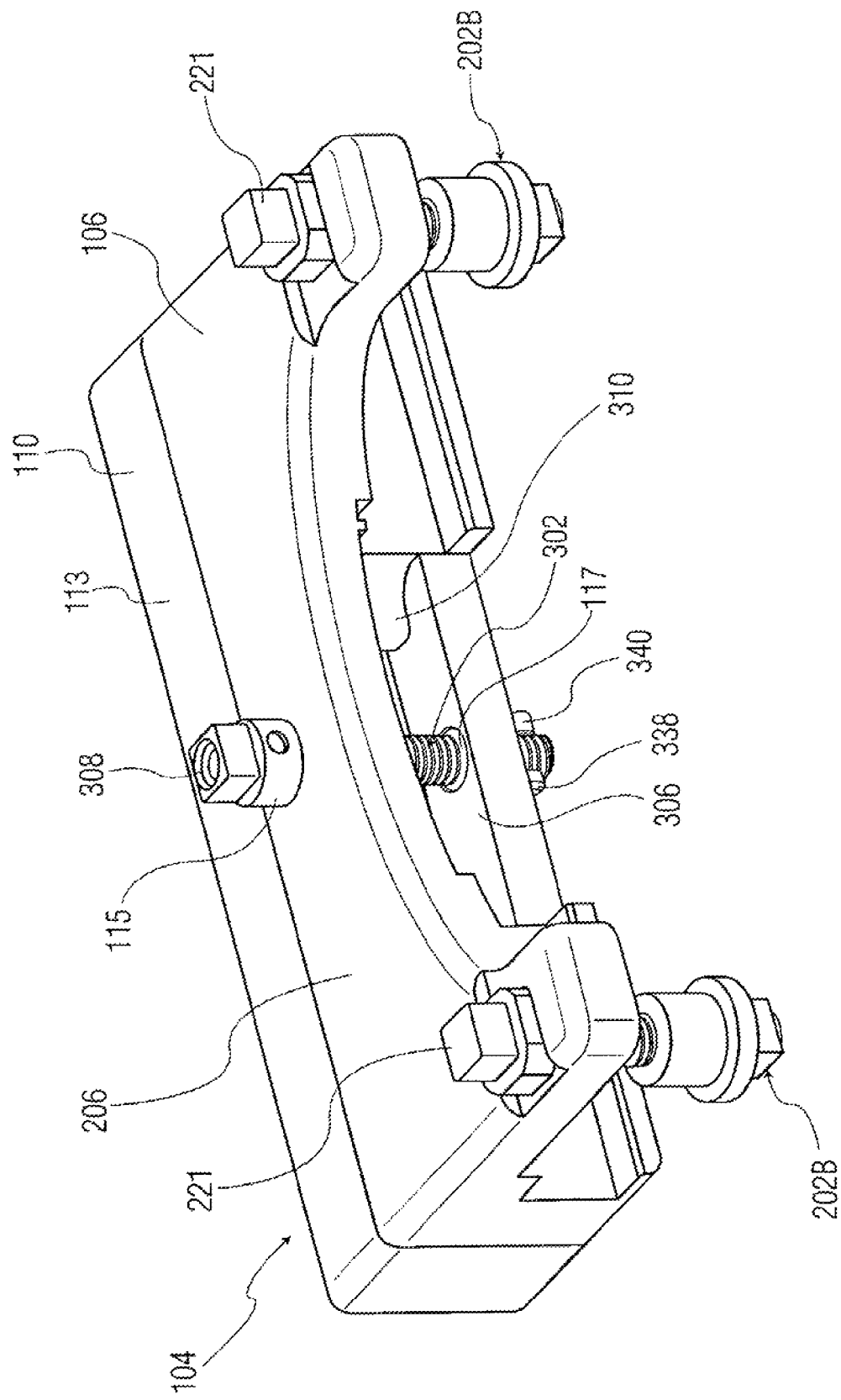

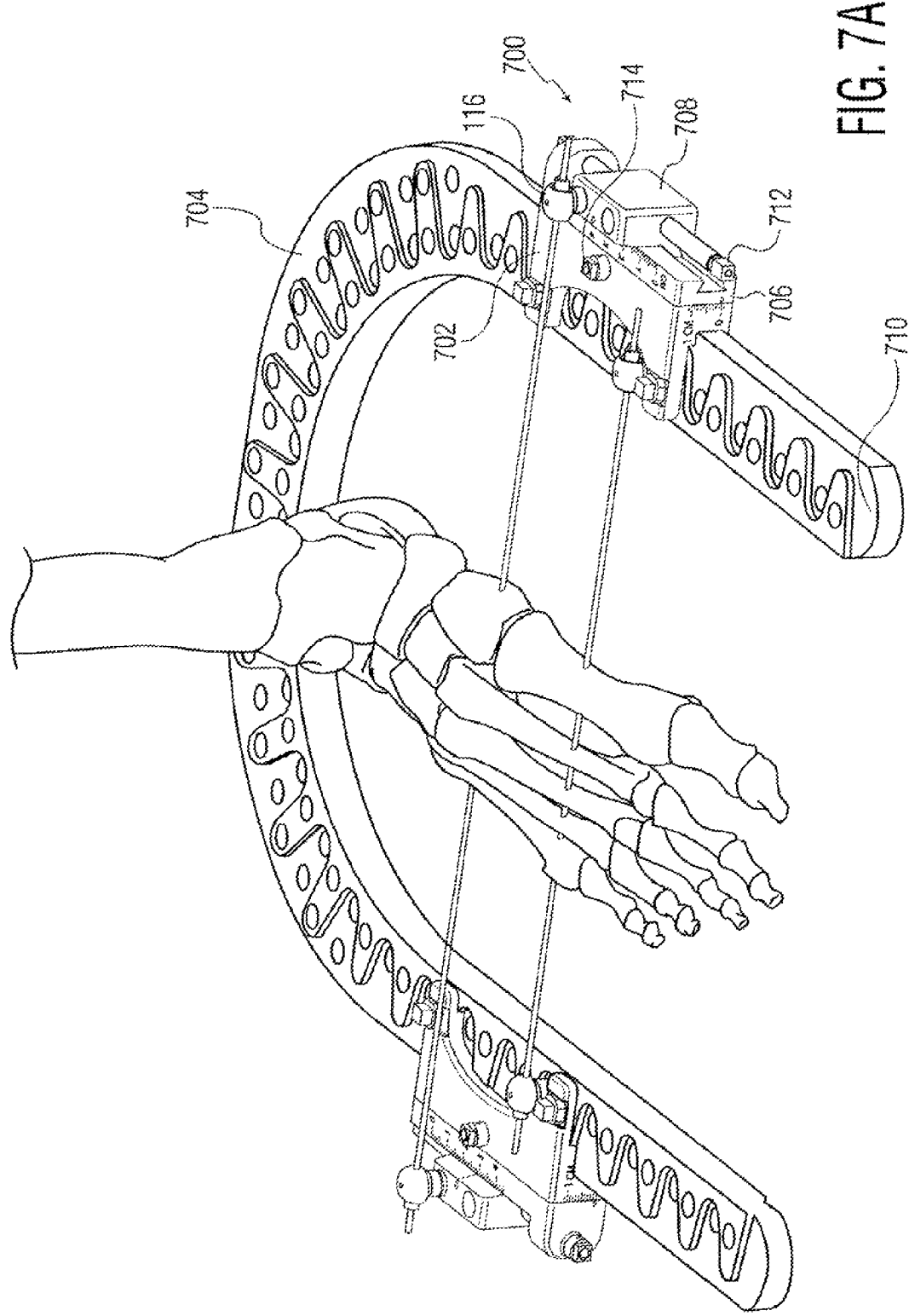

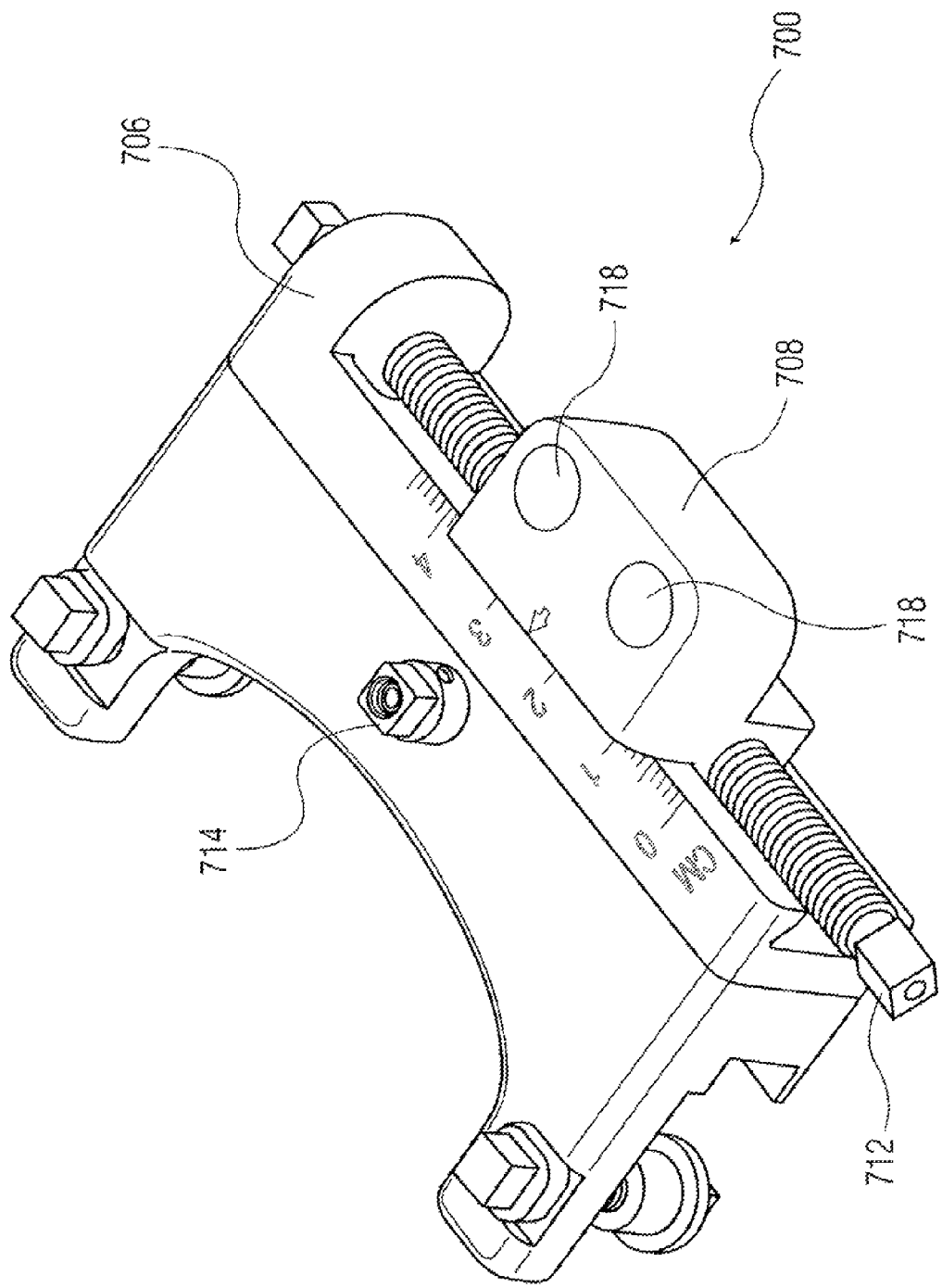

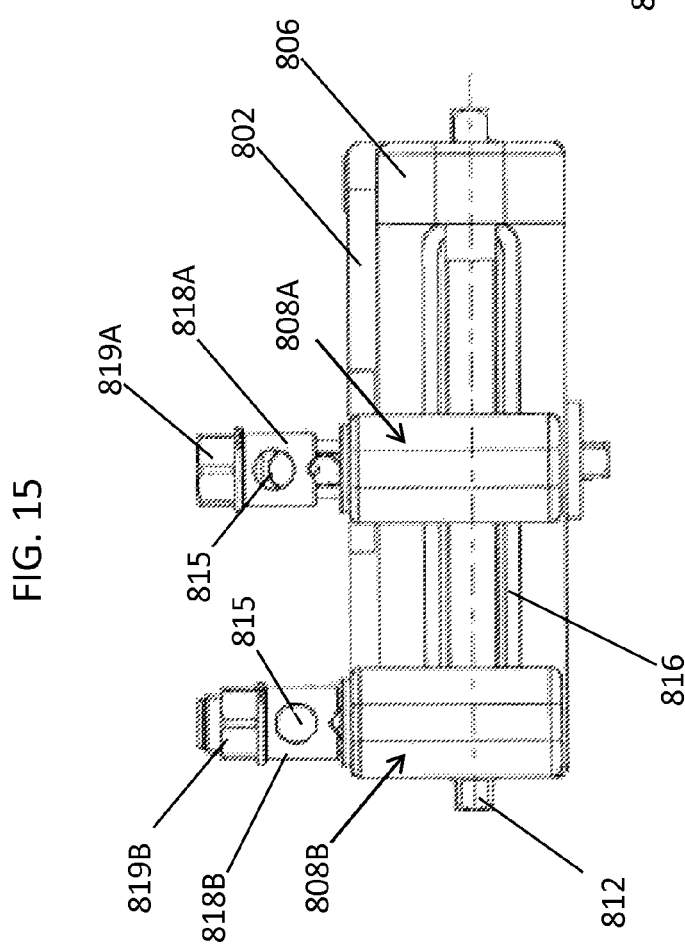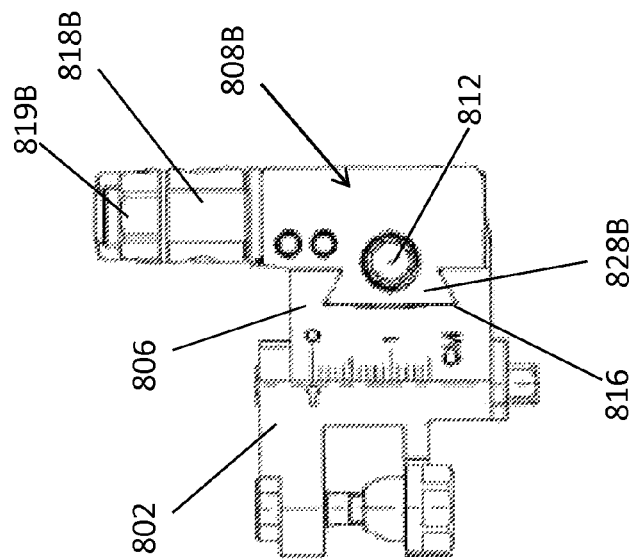

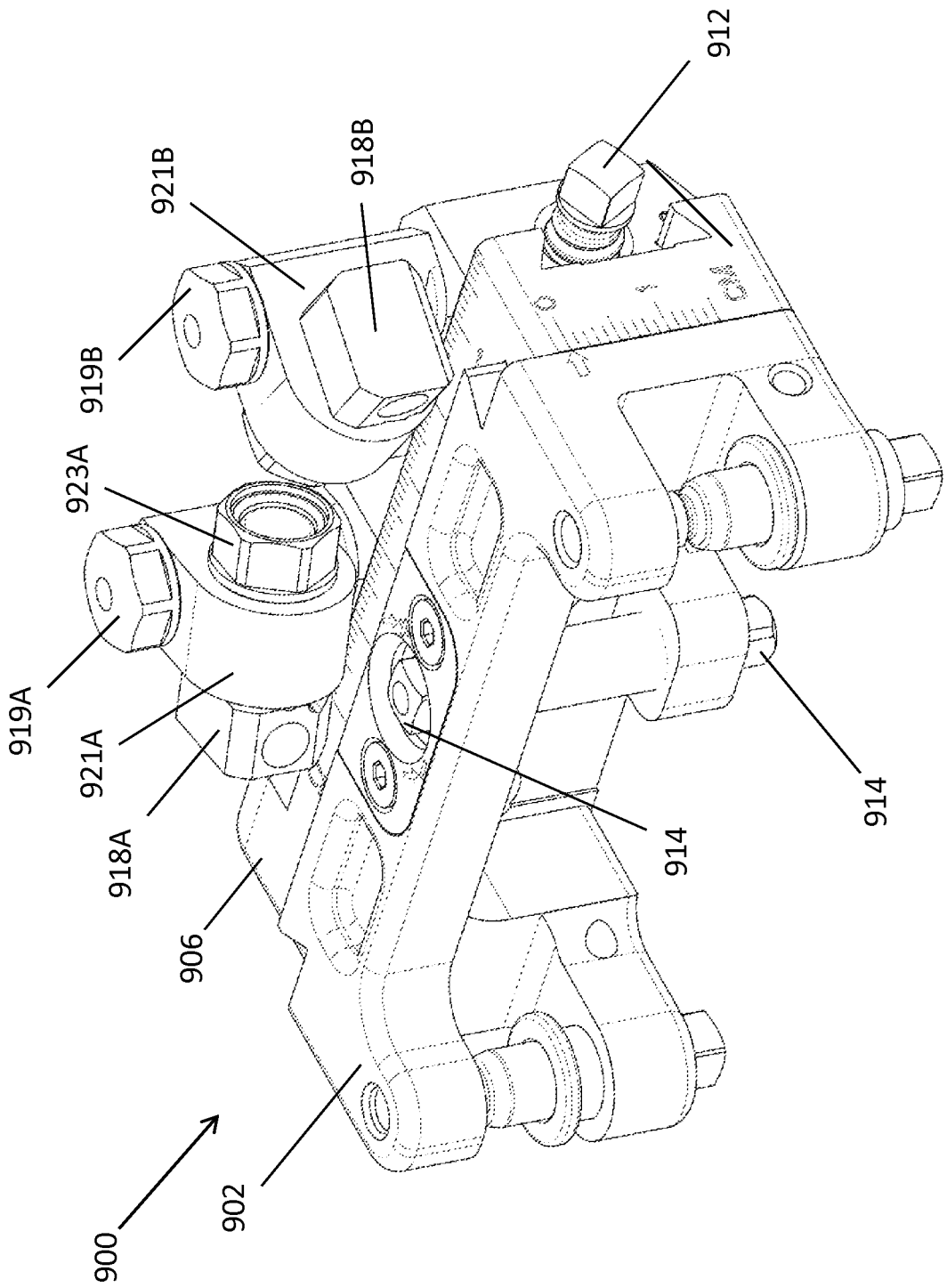

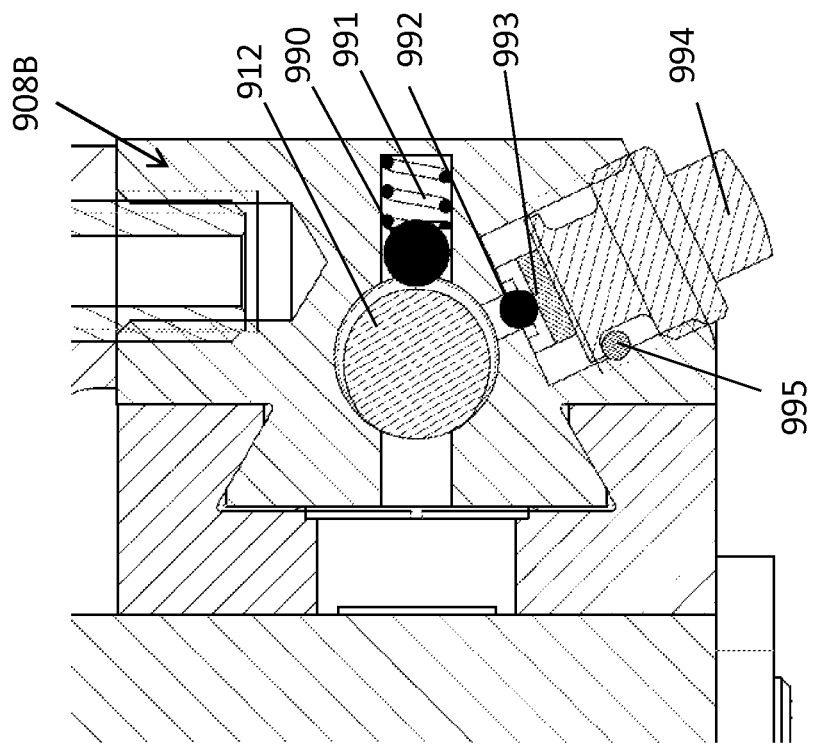
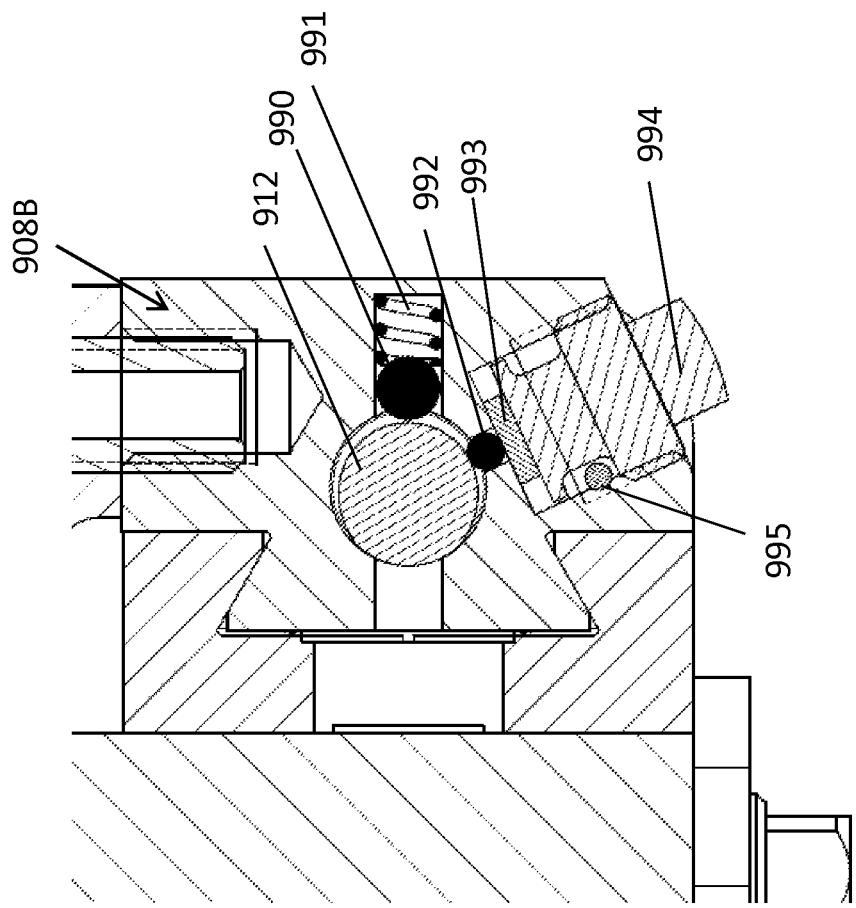

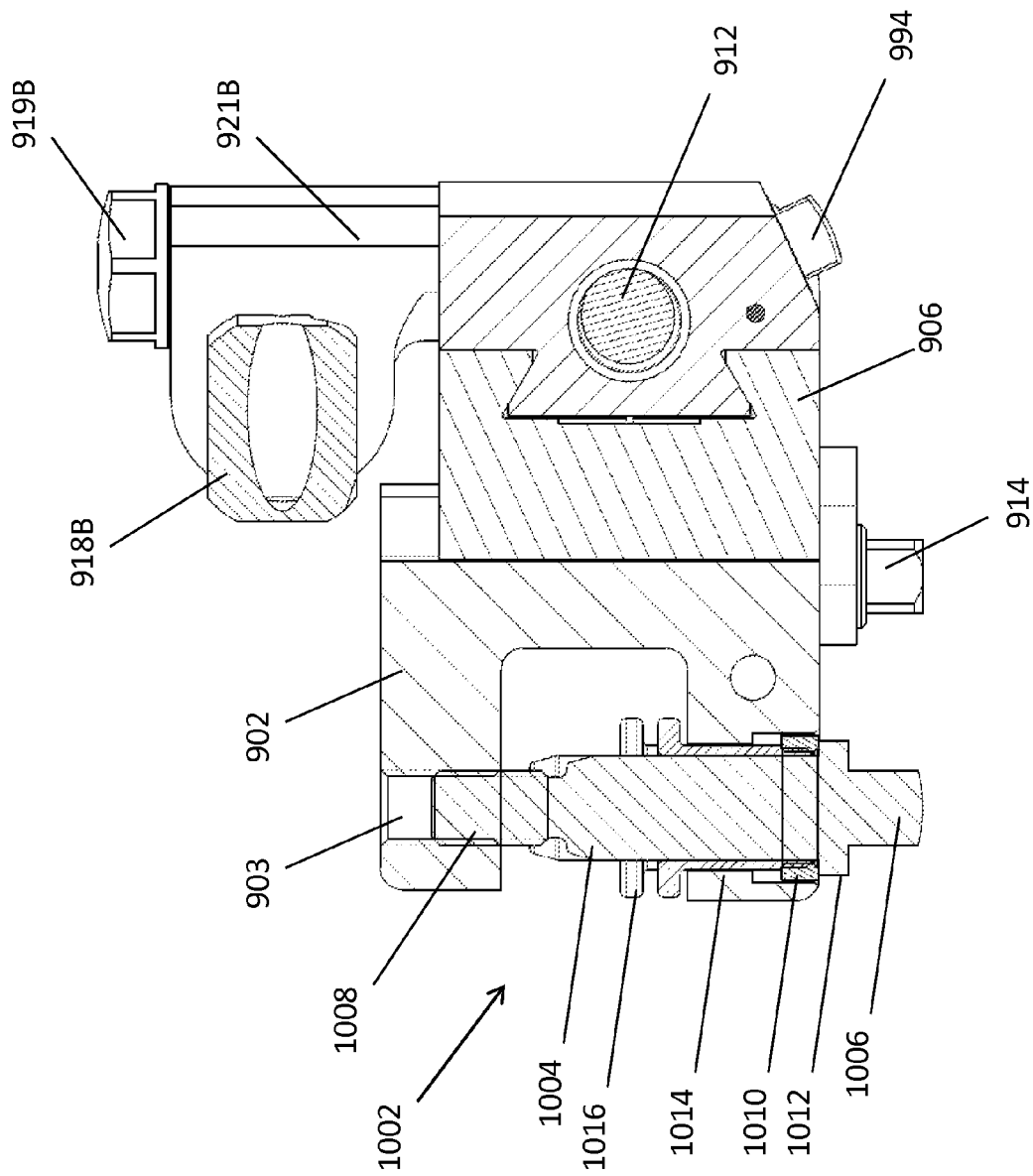

DYNAMIC EXTERNAL FIXATOR AND METHODS FOR USE

CROSS-REFERENCE TO RELATED APPLICATIONS

The present application is a continuation-in-part of U.S. patent application Ser. No. 12/573,310, filed Oct. 5, 2009, the disclosure of which is incorporated herein by reference.

BACKGROUND OF THE INVENTION

During reconstruction of a fractured or broken bone it is necessary to keep the repaired bone in an immobilized and stable state during the healing process. Further, the pieces of broken bones need to be encouraged to grow together. That is, the bone may be broken into multiple pieces and those pieces need to be moved together to promote proper healing. Presently, this is accomplished using a rigid body such as an external fixation ring or frame and various fixation components (e.g., wires, pins, etc.). These fixation components extend from the ring and immobilize the bone and move the bone into proper realignment.

More specifically, the rigid body used in foot and/or ankle reconstruction is a foot frame. Typically, foot frames have an open ring member. This open ring member typically is a single U-shaped frame designed to connect with half pins or wires (e.g., Kirschner or k-wires) passed through the broken or fractured bones. To encourage the bones together, these wires are implanted through particular pieces of the bone (e.g., the foot and/or ankle) and are attached at their ends to the open ring member. These wires are, typically, attached to the open ring member by wire/rod nuts. Further, these wires immobilize and/or apply force to the particular bones in order to move the bones together into proper alignment.

Presently, in order to provide a force to move the bones these wires are bent prior to being attached to the open ring member. Thus, by applying tension to the wire, the wire straightens creating a force on the bone and encouraging the bones together. However, this technique provides little control over the movement of the wire and amount of force on the bone.

Accordingly, a need exists to develop a device and method for accurately moving the wires so as to move the bones together in a controlled manner.

BRIEF SUMMARY OF THE INVENTION

Disclosed herein is an external fixation system. In one embodiment, the external fixation system includes a ring element and an adjustable device. The ring element has a planar surface and a side wall. The adjustable device is mounted on the ring element and includes a body, a first member, and a second member. The body has first and second ends extending outwardly from the ring element and is releasably mounted on the ring element. The first member is mounted on the body and is capable of moving in a direction perpendicular to the planar surface of the ring element by rotation of a first drive screw mounted on the body in engagement with a mating drive element on the first member. The second member is capable of linear motion with respect to the first member and the side wall of the ring element between the first and second ends of the body by rotation of a second drive screw mounted on the first member and in a threaded bore in the second member. The second member can further include a rotatable pin holder configured to mate with a first bone fastener.

The rotatable pin holder of the second member may be configured to rotate about an axis perpendicular to the planar surface of the ring element. The external fixation system may also include a third member capable of linear motion with respect to the first member and the side wall of the ring element between the first and second ends of the body by rotation of a second drive screw mounted on the first member and in a threaded bore in the third member. The third member may further include a rotatable pin holder configured to mate with a second bone fastener. The rotatable pin holder of the third member may be configured to rotate about an axis perpendicular to the planar surface of the ring element.

The linear motion of the second member with respect to the first member may be guided by a protrusion in the second member mated with a recess in the first member.

The external fixation system may also include a rotatable connector extending from the second member and adapted to rotatably mate with the rotatable pin holder. The rotatable connector may be configured to rotate about an axis perpendicular to the planar surface of the ring element. The rotatable pin holder may be configured to rotate about an axis perpendicular to the axis about which the rotatable connector is configured to rotate.

The second member of the external fixation system may also include a locking mechanism. The locking mechanism may include a rotatable member and a locking member. The locking mechanism may be configured to change from an unlocked position to a locked position by rotating the rotatable member. Rotation of the rotatable member may drive the locking member into frictional engagement with the second drive screw. The locking member may be a ball configured to fit between adjacent threads in the second drive screw. The second member, when the locking mechanism is in the unlocked position, may be capable of linear motion with respect to the first member and the side wall of the ring element between the first and second ends of the body without rotation of the second drive screw. The second member may further include a locating ball and a spring biasing the locating ball toward the second screw drive. The locating ball, while the second member is linearly moving with respect to the first member when the locking mechanism is in the unlocked position, may consecutively enter grooves between adjacent screw threads in the second drive screw due to force provided by the spring. The locating ball may provide at least one of auditory or tactile feedback upon entering a groove between adjacent screw threads in the second screw drive.

The body of the external fixation system may further include a first flange and a second flange defining a gap space. The gap space may be configured to receive a portion of the ring element. The external fixation system may additionally include a connector system including a connector, a head at one end of the connector, and a threaded portion at a second end of the connector. The connector may be configured to extend through a hole in the portion of the ring element received in the gap space, and the threaded portion may be configured to threadingly engage an aperture in the first flange. The connector system may further include a nut and a clamp, the nut and the clamp each surrounding portions of the connector. Rotation of the head may advance the threaded portion of the connector through the aperture in the first flange and further advance a flanged end of the clamp into engagement with the planar surface of the ring element.

Also disclosed herein is a method for realigning, compressing, or distracting broken bones. In one embodiment, this method includes providing an external fixation device having a ring member and fixing an adjustable device having a body to the ring member. The adjustable device may have a first member movably attached to the body, a second member movably attached to the first member, a connector rotatably attached to the second member, and a pin holder rotatable attached to the connector. The method also may include inserting a k-wire or half pin through a first piece of bone and affixing the k-wire or half pin to the ring member, and inserting a second k-wire or half pin through a second piece of bone and affixing the second k-wire or half pin to the pin holder of the adjustable device. The method may still further include adjusting at least one of the first and second movable members of the adjustable device with respect to the body by rotating two drive screws in engagement with two mating drive elements formed in each of the first and second moveable members to realign, compress, or distract the broken bones. The first and second moveable members may be adjusted by moving the first member in a direction perpendicular to a plane of the ring member. The second member may be adjusted by linearly moving the second member with respect to the first member.

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

BRIEF DESCRIPTION OF THE DRAWINGS

These and other aspects of this invention are explained and elaborated through reference to the embodiments described as examples below. Examples of embodiments are described in the following with reference to the following drawings.

FIG. 3A is an isometric view of an adjustable device showing the interaction between a first member and a body that enables the first member to move up and down (i.e., perpendicular to a planar surface on the ring element);

FIGS. 7A-7B are isometric views similar to FIGS. 1A and 1B showing the adjustable device from two different positions;

FIG. 8A is an isometric view of an alternate adjustable device allowing two degrees of movement;

FIG. 15 is a rear view of the adjustable device of FIG. 14.

FIG. 16 is a side view of the adjustable device of FIG. 14.

FIG. 20 is a top front perspective view of the device of FIG. 17.

FIG. 21A is a side cross-sectional view of a portion of the device of FIG. 17 in a locked position.

FIG. 21B is a side cross-sectional view of a portion of the device of FIG. 17 in an unlocked position.

FIG. 22 is a side cross-sectional view of the device of FIG. 17.

DETAILED DESCRIPTION

Figure 1A:
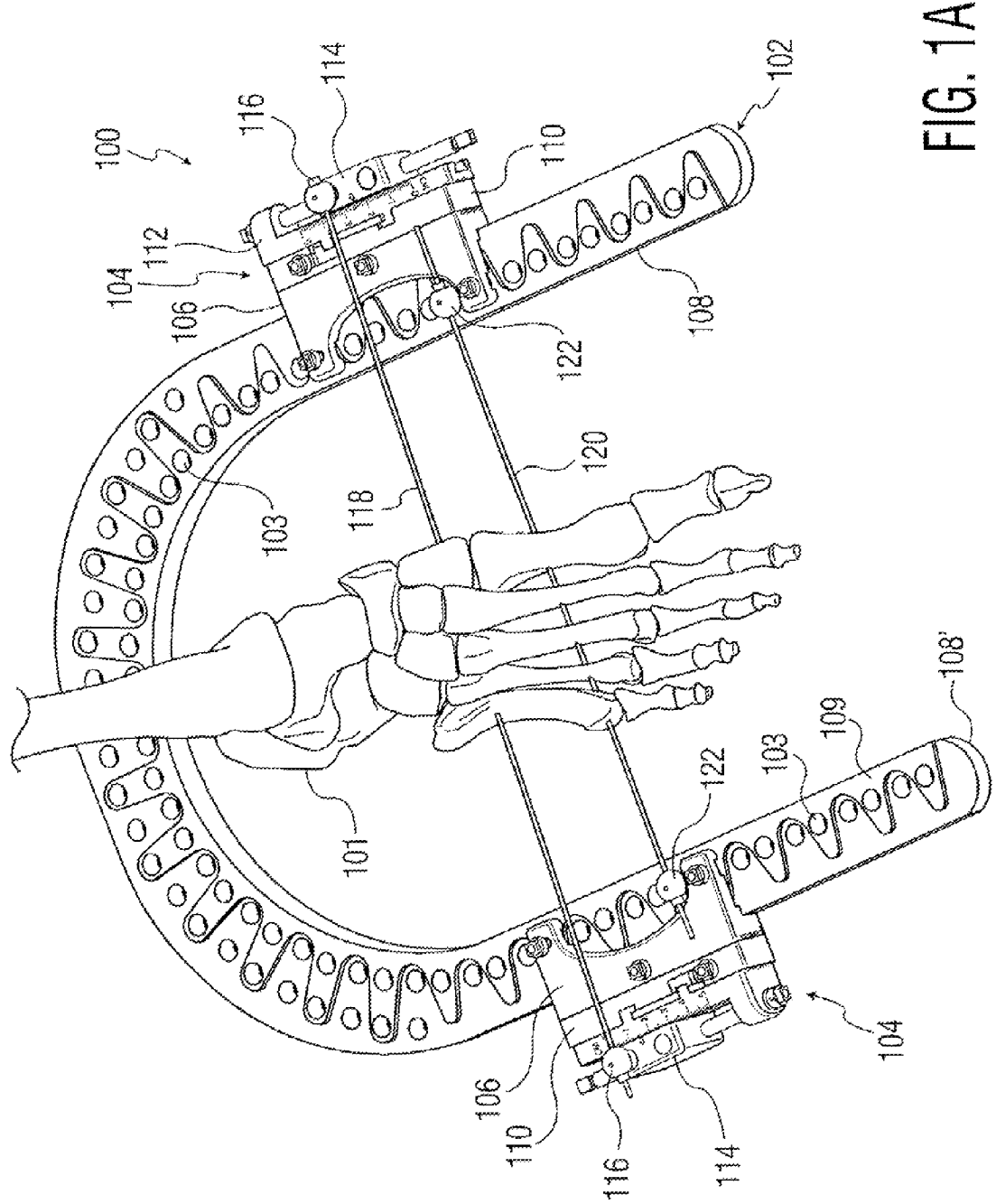
FIGS. 1A-1B show an isometric view of an external fixation device having a ring element and two adjustable devices having k-wires mounted thereon attached to the parts according to the present invention.
Figure 1B:
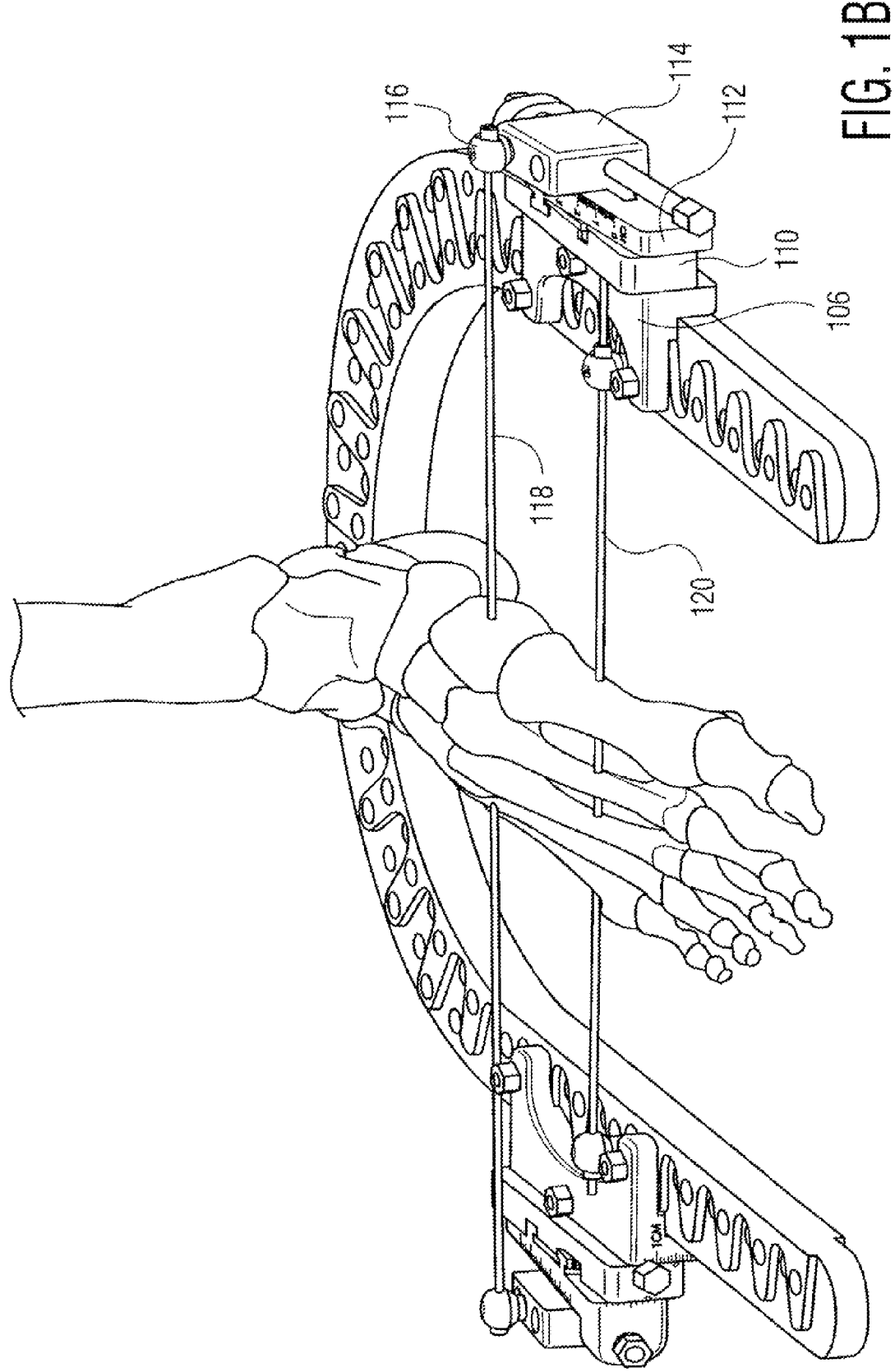

Referring to FIGS. 1A-1B, in accordance with a preferred embodiment of the present invention, an isometric view of a dynamic external fixator generally denoted as 100 is shown mounted on a foot 101 by pins. Dynamic external fixator 100 includes a U-shaped ring element 102 having a plurality of mounting holes 103 with at least one adjustable device 104, and preferably two, releasably attached to a pair of mounting holes 103. Adjustable device 104 includes a body 106 releasably attached to arms 108, 108' of ring element 102. The adjustable device further includes a first member 110 slidably mounted on body 106 capable of providing movement in a direction perpendicular to a proximal surface 109 of arm 108, 108' of ring element 102. Further, a second member 112 pivotally mounts on first member 110 for providing angular movement (i.e., rotation) with respect to first member 110. Further still, a third member 114 mounts on second member 112 providing linear movement along arms 108, 108'. Preferably one or more wire engagement elements 116' attach first or second k-wires 118 that pass through a fractured bone respectively. The wire engagement elements are mounted to third member 114 and/or to ring 102 directly. For example, as shown, first k-wire 118 attaches to a standard bone engagement element 116. Further, a second k-wire 120 can attach directly to ring element 102. For example, as shown, second k-wire 120 attaches to ring element 102 by being clamped in a standard ring engagement element 122 mounted in a hole 103.

Preferably first and second k-wires 118,120 are substantially smooth pins with a drill tip. In some instances, however, first and second k-wires 118,120 may not include a drill tip. Further, first and second k-wires 118,120 can be made of any suitable material, such as, but not limited to, stainless steel, titanium, and titanium alloy. Further, first and second k-wires 118, 120 can connect to bone engagement element 116 and ring engagement element 122 by being inserted through a hole (not shown) in bone engagement element 116 or ring engagement element 122 and applying a force on first or second k-wires 118, 120 by, for example, a set screw (not shown). Alternatively, bone engagement element 116 or ring engagement element 122 can be a wire/rod nut. Any reasonable method for attaching first and second k-wires 118, 120 to bone engagement element 116 or ring engagement element 122 can be used.

Ring element 102 can be a substantially monolithic material designed to releasably attach to at least one adjustable device 104. Ring element 102 can be made of metal (e.g., stainless steel, titanium, etc.), composites (e.g., Carbon PEEK, etc.), or any other material deemed suitable. Further, although described as a u-shaped ring, ring element 102 can include any shape that allows at least one adjustable device to be releasably connected to it. For example, ring element 102 can be a circle shape, horseshoe shape, square shape, rectangle shape, or any other shape deemed suitable. Ring element 102 preferably is planar creating a relatively flat surface on ring element 102. This flat surface is used to provide a flat surface to releasably attach ring element 102 with adjustable device 104. Such a ring can have four levels as shown in U.S. patent application Ser. No. 12/157,612 filed Jun. 11, 2008, the disclosure of which is incorporated herein by reference.

Figure 2A:
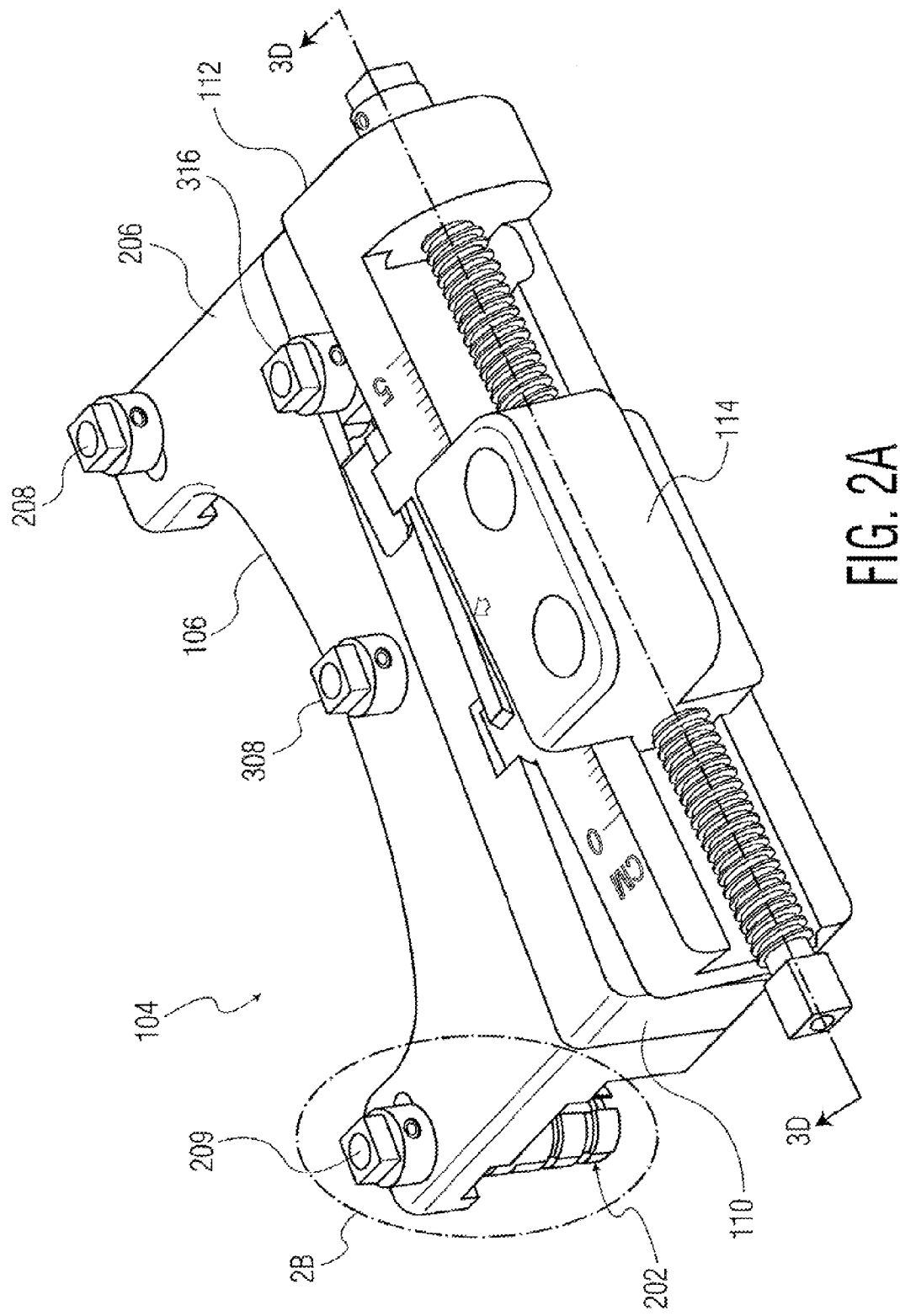
FIG. 2A shows an enlarged isometric view of the adjustable device shown in FIG. 1.

Referring to FIG. 2A, adjustable device 104 is shown in greater detail. Adjustable device 104 has a body 106 with a pair of expandable connectors 202A that releasably connect adjustable device 104 to holes 103 of ring element 102. Attached to body 106 is first member 110 which slidably mounts on body 106. While mounted on body 106, when fixed on ring 102, first member 110 can move up and down with respect to top planar surface 206 of body 106. That is, first member 110 can move in a direction perpendicular to upper surface 206 of body 106 and the plane of the ring 102. This is accomplished by the rotating threaded pin 316 as will be described below. Further, because, in the preferred embodiment, surface 206 of body 106 is parallel to the plane of ring element 102 (see, FIGS. 1A-1B) first member 110 moves in a direction perpendicular to the plane of ring element 102.

Figure 2B:
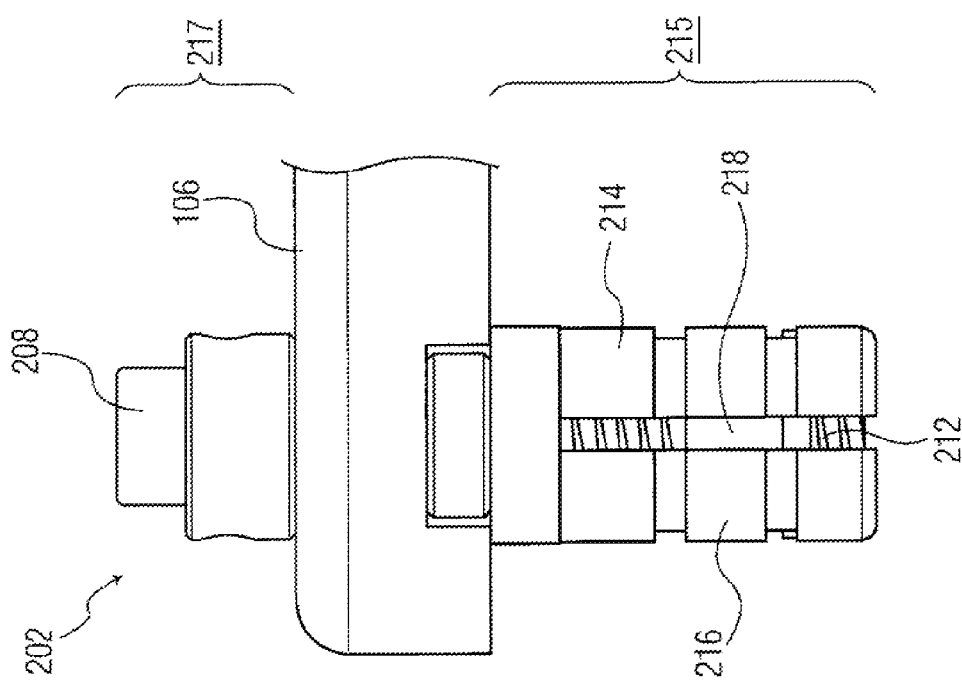
FIG. 2B shows an enlarged view of area A of FIG. 2A showing a ring coupling element.

Referring to FIG. 2B an exemplary ring element connector is displayed. As shown, preferred connector 202A includes a lower outer portion 215 located under body 106 split into two sections 214, 216 and an inner portion 217 with a drive head 208 located above body 106 for engaging a drive tool. Further, inner portion 217 has a threaded shaft 212 coupled to drive head 208 and extends between the two halves 214, 216. Threaded shaft 212 includes tapered nut 218 which when moved toward body 106 caused sections 214 and 216 to expand. After connector 202A is placed through body 106 and into hole 103 in the ring element 102, nut 218 is threaded on the bottom of threaded shaft 212. As drive 208 is rotated nut 218 causes the two halves 214,216 to expand thereby securing the adjustable device to the ring element. Although described as two halves the split portion can include any number of sections (e.g., three or four sections).

Figure 2C:
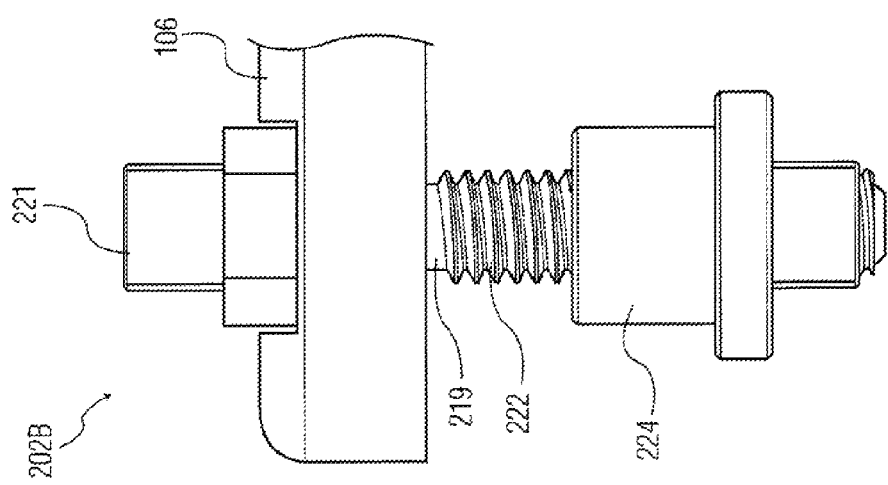
FIG. 2C is an enlarged view of an alternate ring coupling element of the present invention used in FIG. 3A.

Referring to FIG. 2C there is shown an alternative ring element connector 202B. As shown, ring connector 202B can include a shaft 219 with a screw thread portion 222 and a drive head 221. The threaded shaft portion 222 is inserted through the bore in body 106 until drive head 221 comes into contact with upper surface body 106. Threaded shaft portion 222 is further inserted through an opening 103 in ring element 102 and threaded into a nut 224. As threaded shaft portion 222 is threaded into nut 224 adjustable device 104 is secured onto ring element 102. Further, any method of releasably securing adjustable device 104 to the ring element can be used. For example, the adjustable device can be releasably attached to the ring element by a screw and nut, a bolt assembly, or any other securing method deemed suitable.

Referring to FIG. 3A, a rear view of two parts of the preferred adjusting device 104 is shown. The two parts are members 110 and 106. First member 110 has a first portion 113 and a central portion 306 which can move in a direction perpendicular to the plane of ring element 102 by rotating a screw shaft 302 via drive head 308. Screw shaft 302 is placed through a hole 115 in body 106 and is threaded into a second threaded hole 117 located in central flange 306 extending rearwardly from first portion 113 of first member 110. Shaft 302 has an end 338 with a pin 340 to ensure the assembly does not come apart during use. In use, a user rotates a drive head 308 causing screw 302 to thread into the second hole thereby moving first member 110 up and down with respect to body 106 (i.e., perpendicular to planar surface 206 of body 106 and perpendicular to the plane of ring element 102). Alternatively, although screw shaft 302 is described as threaded into a second hole in member 110, screw 302 may thread into a threaded hole in body 106 and fixed in part 306. It will be understood that any method of making first member 110 move up and down with respect to body 106 can be used. Further, increasing the number of threads on screw shaft 302 increases the number of rotations needed to move first member 110 up and down. Thus, increasing the number of threads increases the precision of up and down movement.

In some embodiments, flange 306 extending from first member 110 is designed to ride along a protruding track 310 extending from body 106. Riding on track 310 reduces the amount of movement in an undesired direction. Further, any method of mating first member 110 with body 106 designed to decrease movement in an undesired direction can be used. For example, first member 110 and body 106 can include any male-female mating features (e.g., tongue and groove or dovetail) for providing guided movement up and down.

Figure 4:
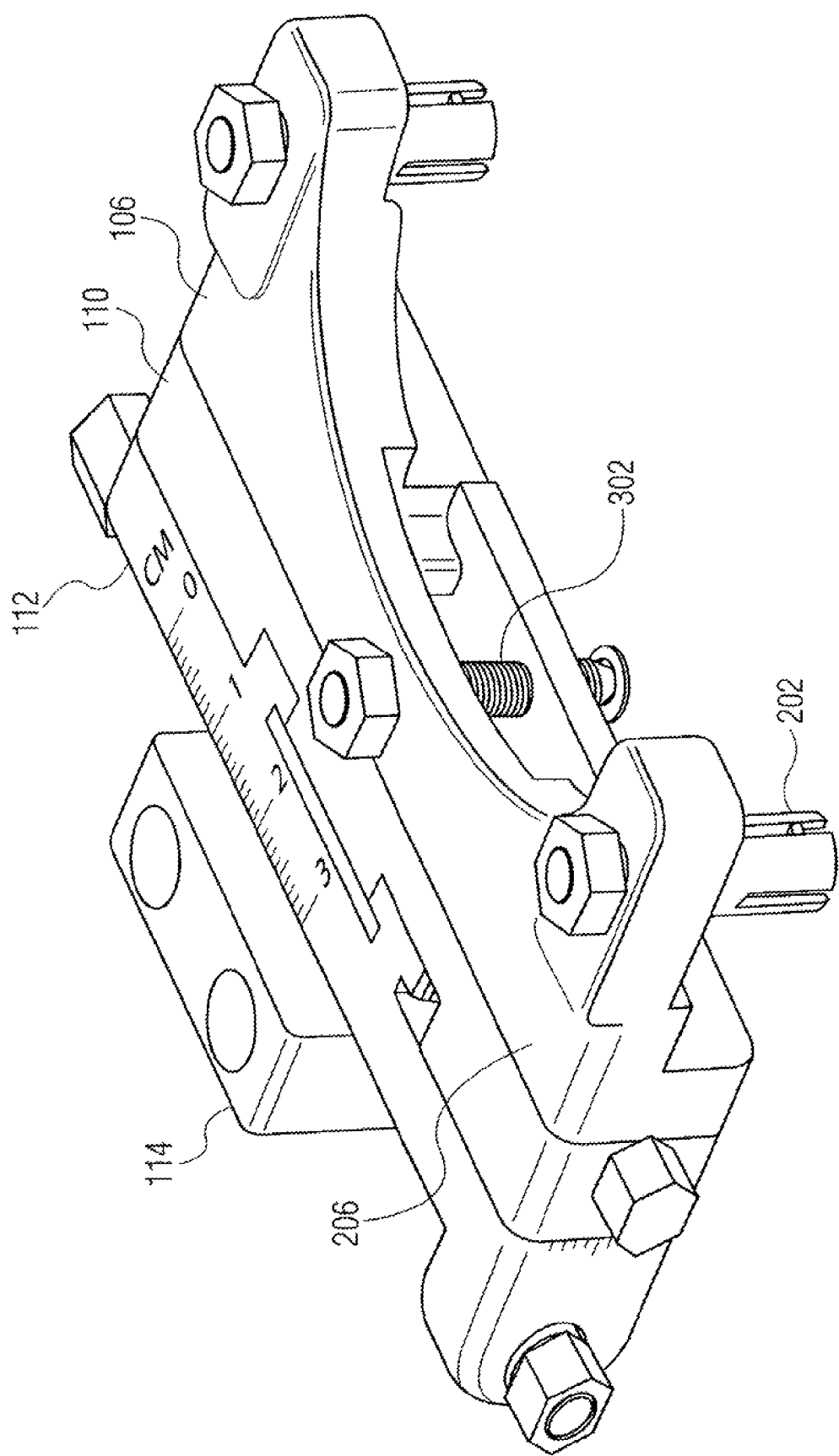
FIG. 4 is a rear view of the adjustable device of FIG. 4 in a first position.
Figure 6A:
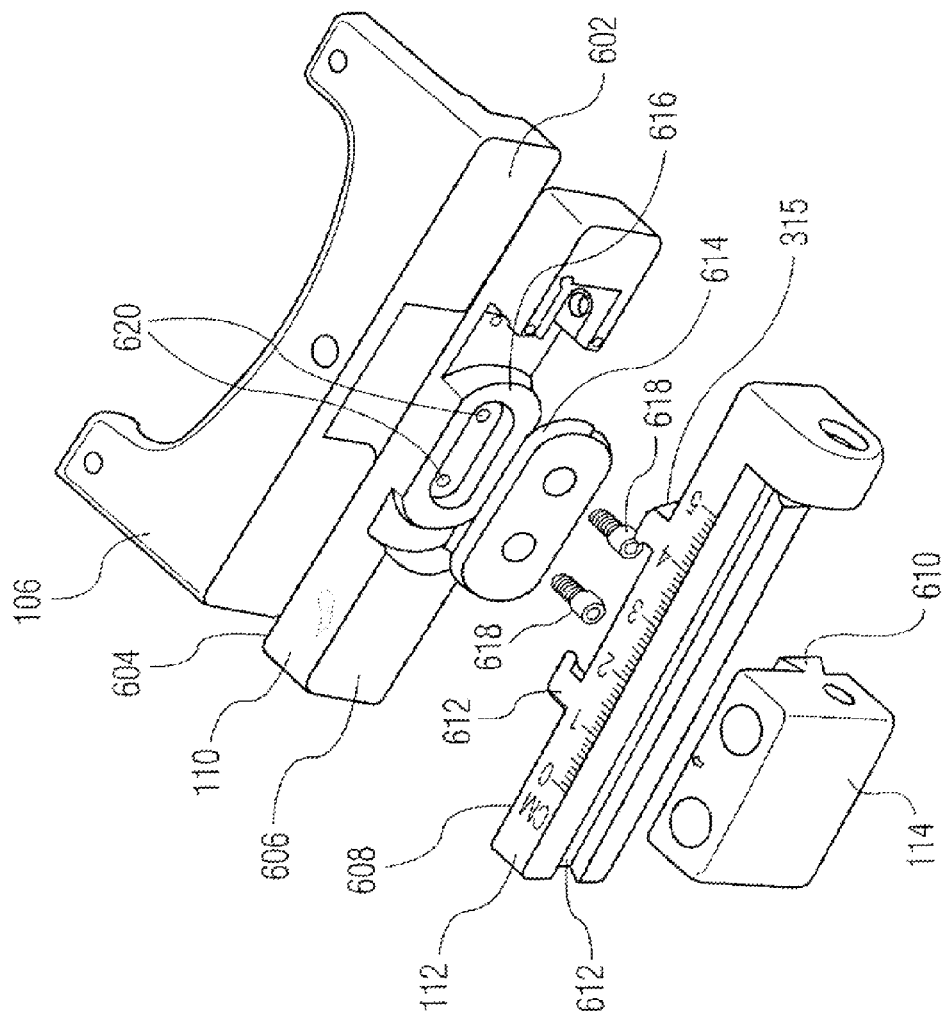
FIGS. 6A and 6B are exploded views of an adjustable device of FIG. 2A showing the body, the first member, the second member, and the third member.

Referring to FIGS. 2A, 4 and 6A, second member 112 is rotatably mounted on first member 110. While mounted on first member 110, second member 112 can rotate through a range of angles with respect to first member 110. That is, second member 112 is pivotally mounted by guide tracks 612 on first member 110 and can rotate with respect to first member 110. For example, in the preferred embodiment, second member 112 can pivot up to 120 degrees around its center on guide 614 mounted on first member 110 as shown in FIG. 6A. That is, second member 112 can, for example, rotate 60 degrees from parallel in an upward direction and 60 degrees in a downward direction with respect to surface 306.

Figure 3B:
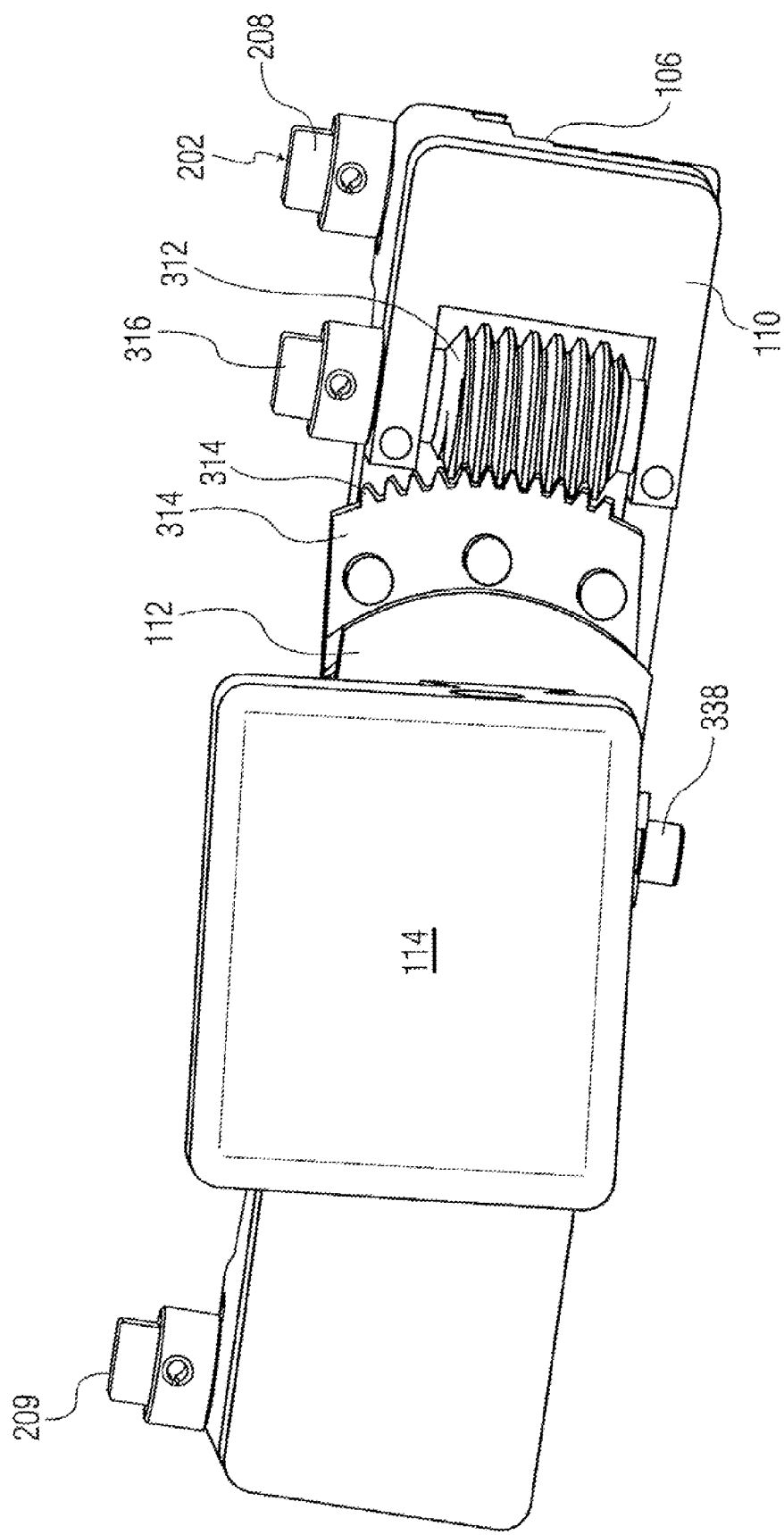
FIG. 3B is an isometric view from lines 3-3 of FIG. 2A and shows the internal gearing that enables a second member to pivot with respect to the ring element.

Referring to FIG. 3B in the preferred embodiment, second member 112 rotates through a range of angles by the interaction of a worm 312 (i.e., a gear in the form of a screw) with an arcuate worm gear 314 mounted on second member 112 on the outer surface of the portion thereof forming track 612 (i.e., a worm wheel). For example, worm 312 can thread into worm gear 314 causing second member 112 to rotate relative to first member 110. In use, a user rotates drive head 316 of worm 312 causing worm 312 to rotate while engaged with worm gear 314. Because first member 110 is attached to body 106 that is fixed to ring element 102, rotating worm 312 while engaged with worm gear 314 causes second member 112 to rotate upwardly or downwardly with respect to the plane of ring 102. Although described as a worm gear and worm any reasonable method can be used to change the angle of second member 112 with respect to first member 110. For example, the angle can be changed by spur gears, helical gears, double helical gears, bevel gears, crown gears, or any other gearing deemed suitable. Further increasing the number of threads (i.e., increasing the number of threads on the worm gear and worm) increases the number of rotations of user interface 316 required to move through a given angle. Thus, increasing the number of threads provides a greater level of precision during rotation.

Referring to FIGS. 2A and 6A, as shown, third member 114 is mounted on second member 112. While mounted on second member 112, third member 114 can move linearly with respect to second member 112. That is, third member 114 can linearly move along arms 108, 108' of the ring element in a direction parallel to the plane of ring 102 in an anterior-posterior direction.

Figure 3C:
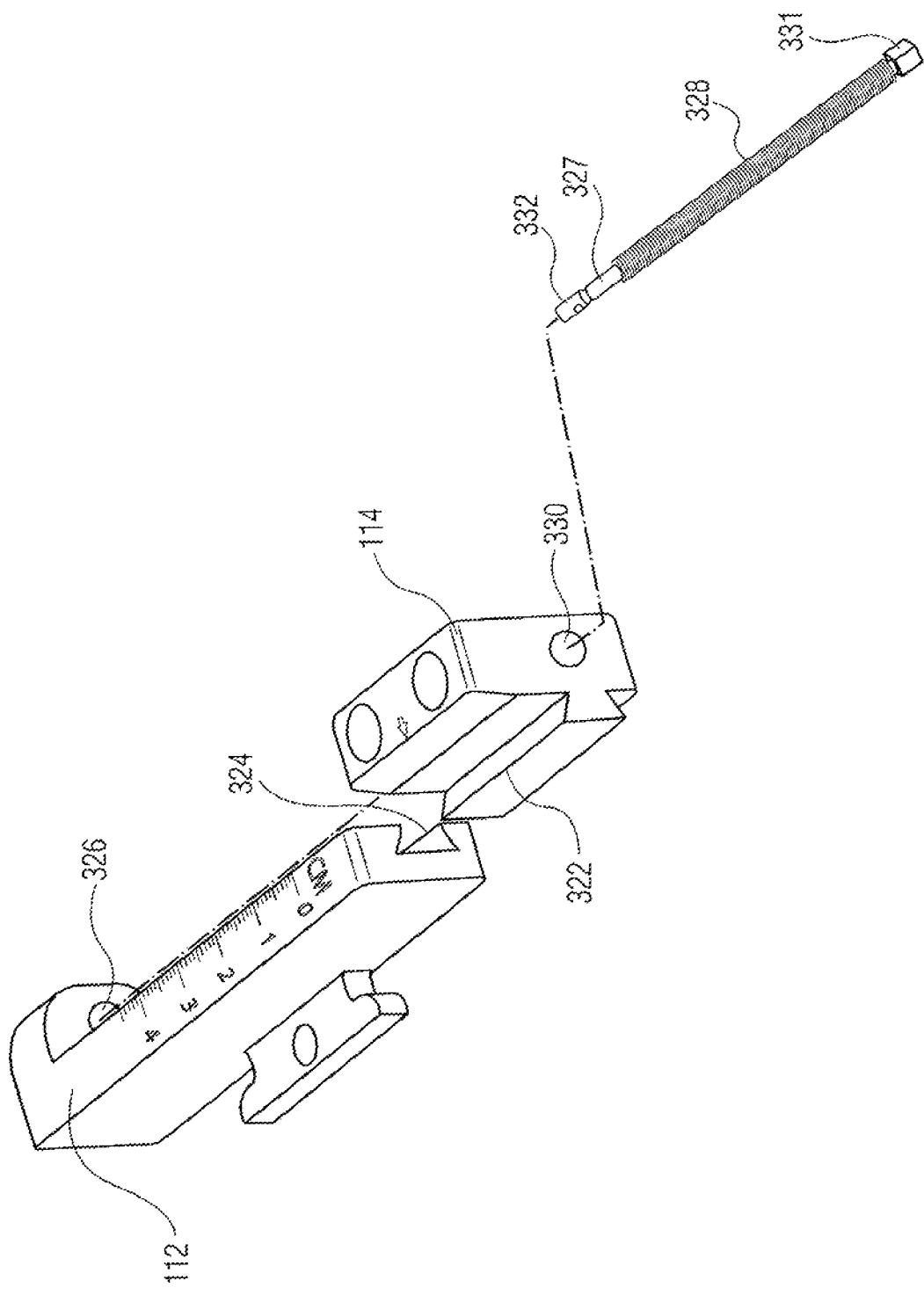
FIG. 3C is an exploded view of the moveable third member and second member shown in FIG. 2A as well as a threaded rod that enables the third member to move linearly with respect to the circumference of the ring element.

Referring to FIG. 3C in the preferred embodiments, third member 114 includes a dovetail protrusion 322 (i.e., guide element) that mates with a groove 324 extending along second member 112. Protrusions 322 mates with groove 322 thereby providing a guide for the linear motion. For example, in the preferred embodiment, a male dovetail protrusion 322 extending from third member 114 can mate with a female dovetail 324 located on second member 112 thereby providing a linear guide between second member 112 and third member 114. Any form of male and female guide elements can be used to provide a linear guide between third member 114 and second member 112.

Figure 3D:
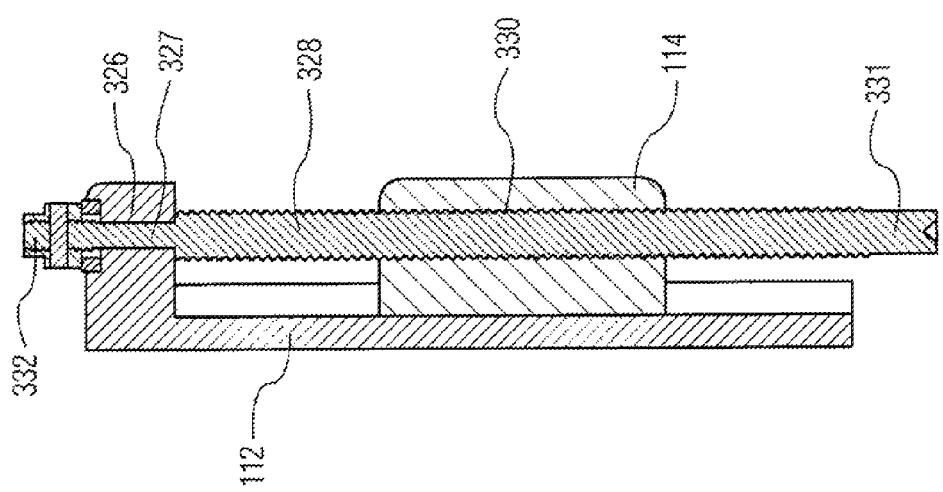
FIG. 3D is a cross-sectional view showing the member of FIG. 3C assembled.

Referring to FIGS. 3C and 3D, in the preferred embodiment, second member 112 includes a bore 326 for receiving an end 327 of a threaded rod 328. Further, third member 114 can translate on threaded rod 328 as it is rotated via drive head 331 or 332. Translation is possible because third member 114 includes a threaded bore 330 for receiving threaded rod 328. Thus, rotating threaded rod 328 translates third member 114 along the axis of threaded rod 328. In use, a user rotates drive head 331 or 332 causing threaded rod 328 to rotate in bore 333 of third member 114 thereby causing third member 114 to move linearly along arm 108, 108' of ring element 102. Alternately, any reasonable method for moving third member 114 linearly can be used. Further, increasing the number of threads/grooves on third member 114 and the number of threads/grooves on rod 328 increases the amount of precision in linearly moving third member 114. In the preferred embodiment, one rotation moves member 114 about one millimeter.

Referring to FIG. 4, the adjustable device having the first, second, and third member in a first position is illustratively depicted. As shown, first member 110 has not moved perpendicular to planar surface 206 of body 106. Further, second member 112 has not been rotated with respect to first member 110. Lastly, third member 114 is depicted in a first position.

Figure 5:
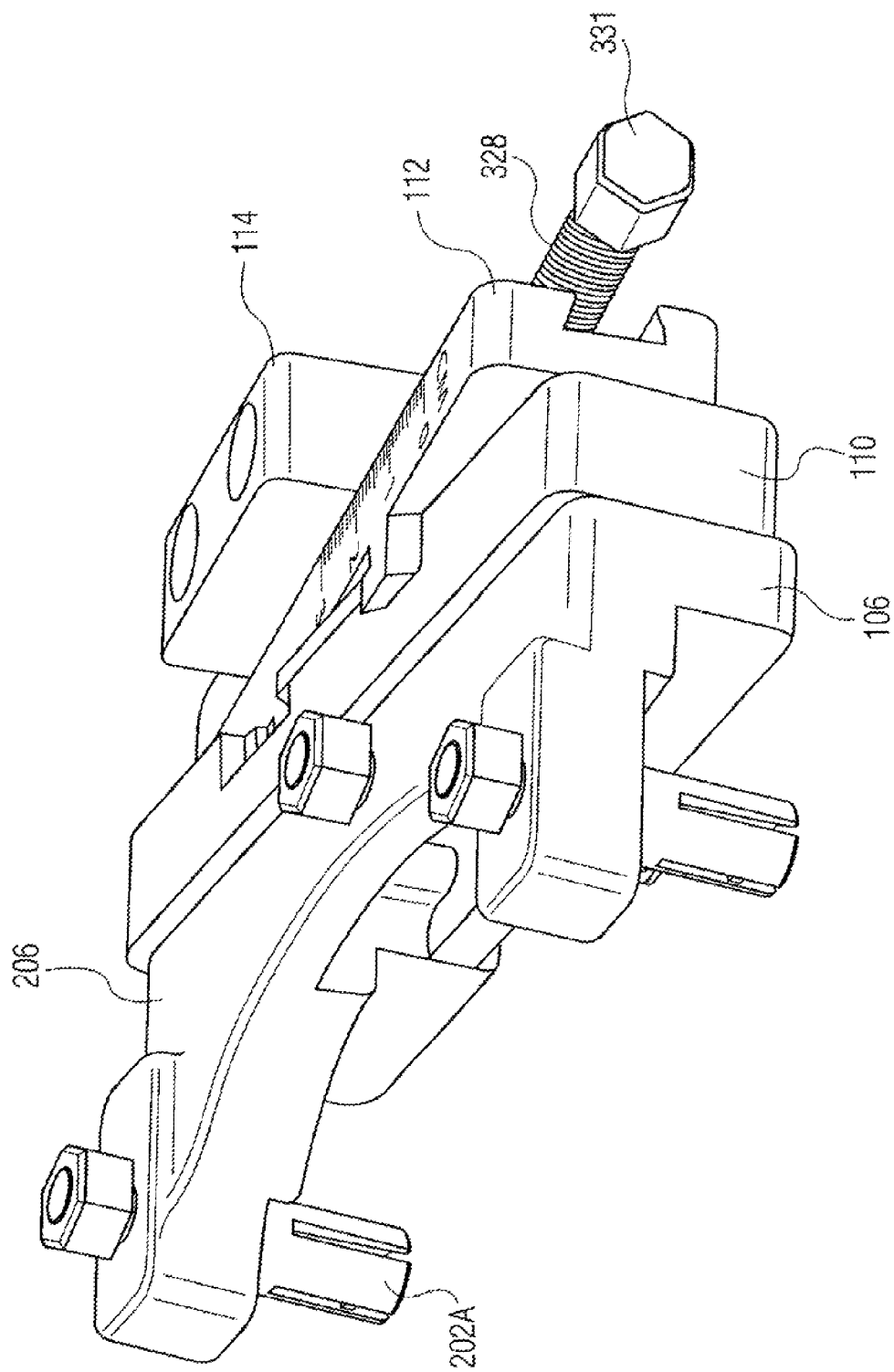
FIG. 5 is an isometric end view of the adjustable device of FIG. 4 in a second position.

Referring to FIG. 5, the relative displacement of each of the first, second, and third members is illustratively depicted as compared to FIG. 4. As shown, first member 110 has been displaced perpendicularly to planar surface 206 of body 106. Further, second member 112, has rotated with respect to first member 110. Lastly, third member 114 is depicted in a second position where it has moved linearly with respect to second member 112.

Figure 6B:
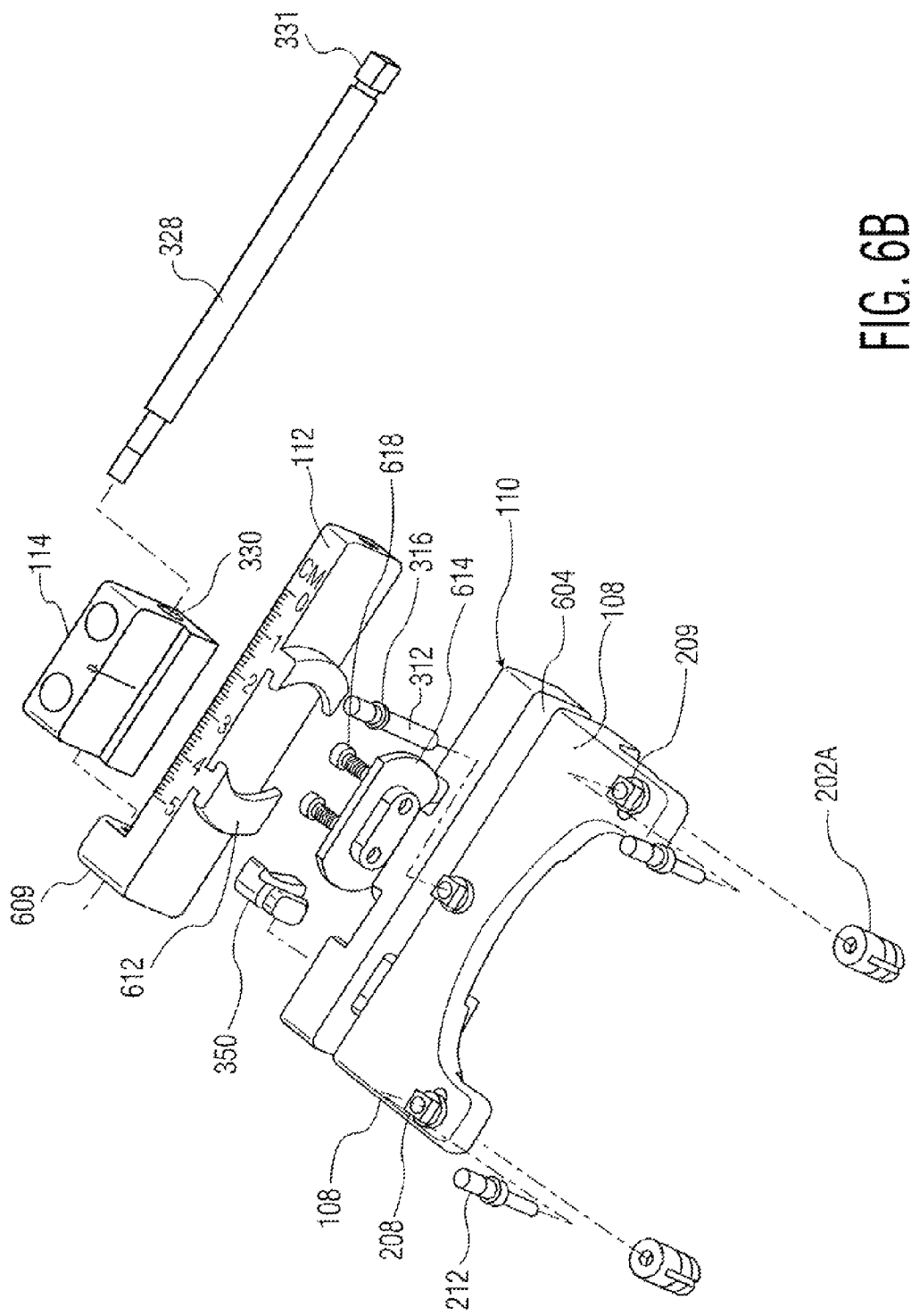

Referring to FIGS. 6A and 6B, there is shown an exploded view of adjustable device 104 of the preferred embodiment illustratively depicts the internal contact surfaces for each of body 106, first member 110, and second member 112. As shown, body 108 includes internal planar surface 602 which contacts internal planar surface 604 of first member 110. These planar surfaces provide a guide surface as first member 110 is displaced in a direction perpendicular to the plane of ring 102. Preferably, internal planar surfaces 602, 604 are substantially smooth surfaces permitting low friction sliding movement. Alternatively, in other instances, internal planar surfaces 602, 604 can include male and female protrusions (not shown) for allowing movement only perpendicular to planar surface 206 of body 106.

Further, as shown, internal planar surface 606 of first member 110 contacts an internal planar surface 608 of second member 112. Thus, during rotation these guide surfaces minimize motion in an undesired direction. Further, the angular motion of second member 112 is guided by track 612 which is in the form of an arcuate guide surface that rides on an arcuate guide element 614 which is attached to a planar surface 616 located on first member 110. Further, track 612 provides a center of rotation centrally located on first member 110. Disc 614 attaches to planar surface 616 by, for example, screws 618 threaded into holes 620 located in first member 110. Because track 612 rides on disc 614 motion in any direction other than the desired angular rotation direction is minimized. Gear teeth 315 are provided on the outer surfaces of track 612 which are driven by worm 312. A lock element 350 may be provided to lock second member 112 in the desired angular position.

Further, third member 114 includes a male dovetail protrusion 610 that mates with a female guide surface 609 acting as a guiding surface when third member 114 moves linearly. Each of the above described surfaces increase the control of the adjustable device by minimizing motion other than in the desired directions.

Figure 7B:
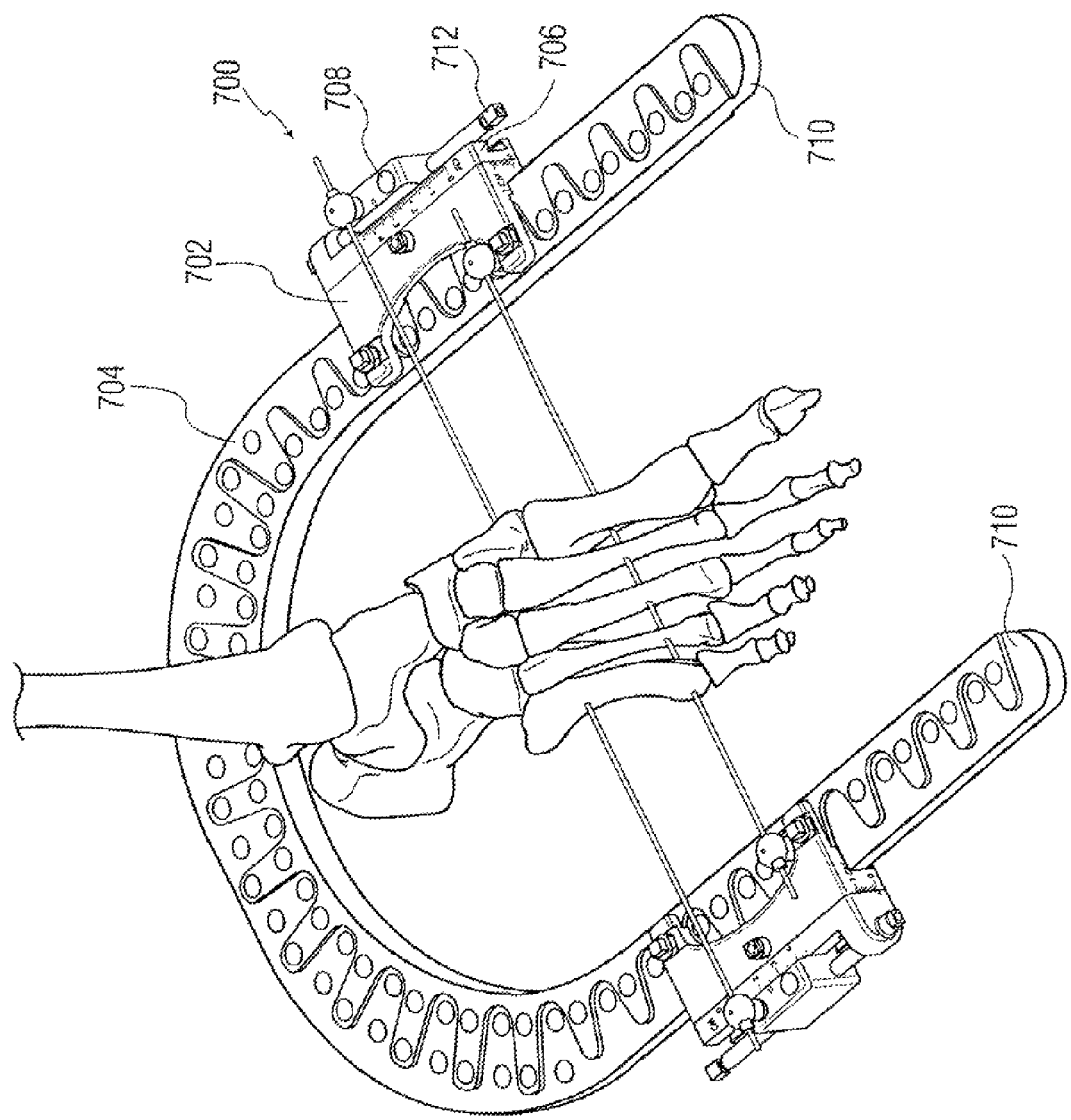

Referring to FIGS. 7A-7B, in some embodiments, adjustable device 104 can move only in the anterior-posterior and inferior-posterior directions. As shown, an alternate adjustable device 700 can include a body 702 attached to a ring element 704. Further mounted on body 702 is a first member 706 providing movement perpendicular to body 702 by rotation of screw 714 and a second member 708 mounted on first member 706 providing linear movement along arms 710 of ring element 704 by rotation of screw 712. In this embodiment there is no rotational movement between member 706 and 702.

As shown, unlike the preferred adjustable device capable of motion in three directions, the adjustable device of FIGS. 7A and 7B is only capable of movement in two directions. As depicted, first member 706 mounted on body 702 provides movement perpendicular to body 702. Further, second member 708 mounted on first member 706 provides motion parallel to the plane of the ring.

Further, in some embodiments, a scale can be located on at least one of first member 110 and second member 112. This scale can be used to determine the length of angular or linear displacement by the member. Further, a scale can be located on any of the body, first member, second member, or third member for respectively determining the amount of linear, angular, or circumferential movement of each of the members.

Figure 8B:
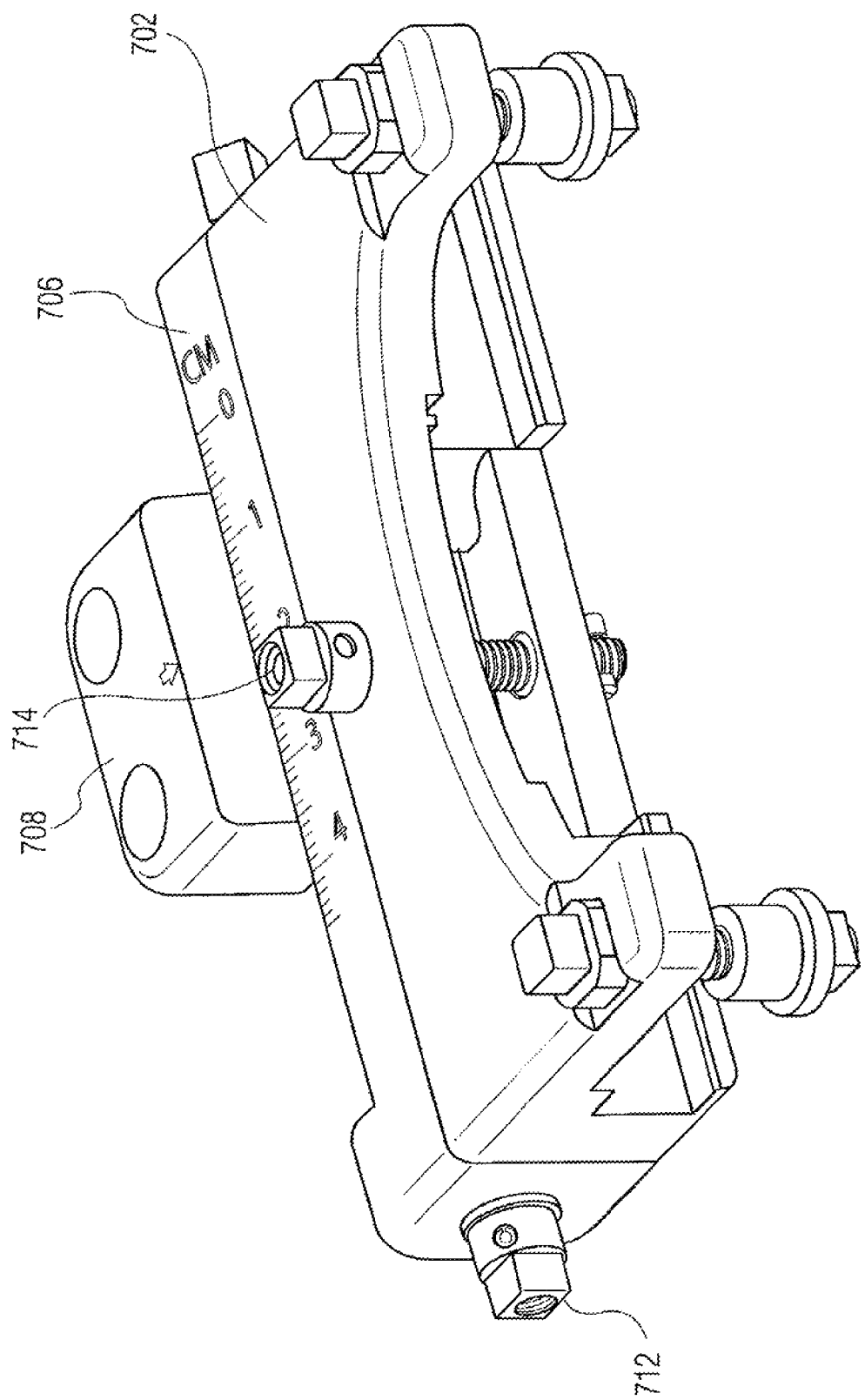
FIG. 8B is a side isometric view of the alternate adjustable device of FIG. 8A.
Figure 9:
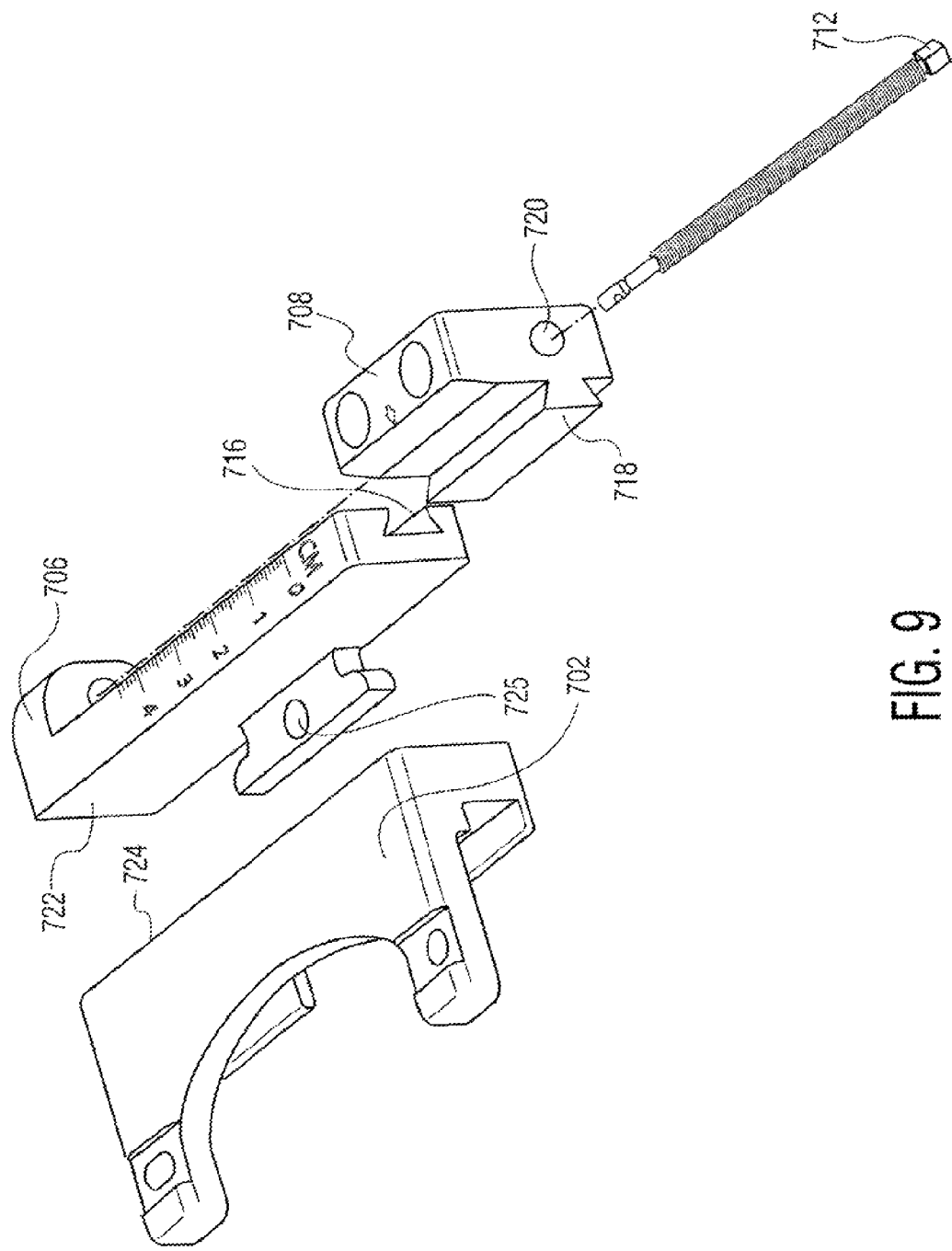
FIG. 9 is an exploded view of the alternate adjustable devices of 8A and 8B.

Referring to FIGS. 8A-9, there is shown an alternate adjustable device as shown in FIGS. 8A and 8B. The device generally denoted as 700 includes a body 702, first member 706 and second member 708 but does not provide rotational movement between member 706 and 702 as in adjustable device 104 (FIG. 5). Movement parallel to the ring is accomplished by turning screw shaft 712 to move element 708 and movement perpendicular to the ring is accomplished by turning screw shaft 714 and moving element 706 in relation to body 702. Pin holder can be located in one or both of holes 718.

FIG. 9 shows an exploded view of the alternate adjustable device 700 including body 702 and element 708 slidably mounted in a groove 716 in member 706 via a dovetail extension 728 and sliding element 708. Again, screw 712 is rotated in a threaded bore 720 of element 708 to cause the movement of element 708 parallel to the ring arm 710. Element 706 and body 702 includes contacting surfaces 722 and 724 respectively. These surfaces contact when the element 706 is moved in a direction perpendicular to the plane of the ring by turning screw 714 in threaded bore 725. This movement may be guide by tongue and groove interconnection as in device 104.

Figure 10:
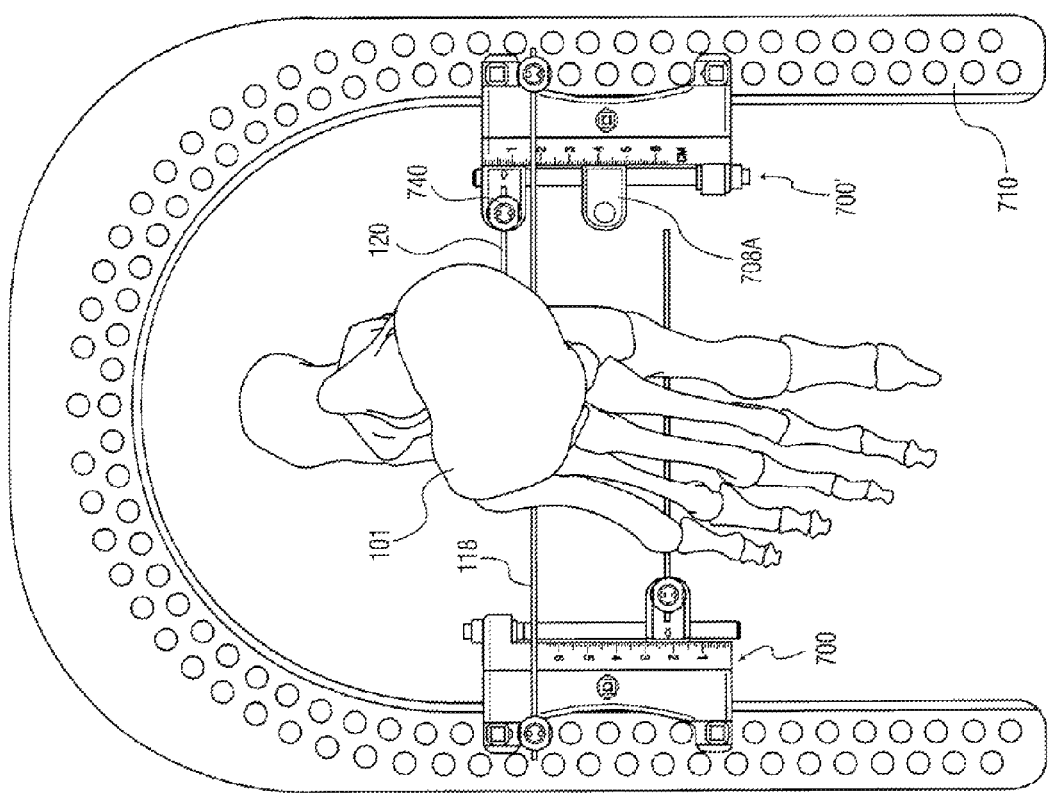
FIG. 10 is a top view of an alternate dynamic external fixator with adjustable members mounted on the inside of the rings.
Figure 11:
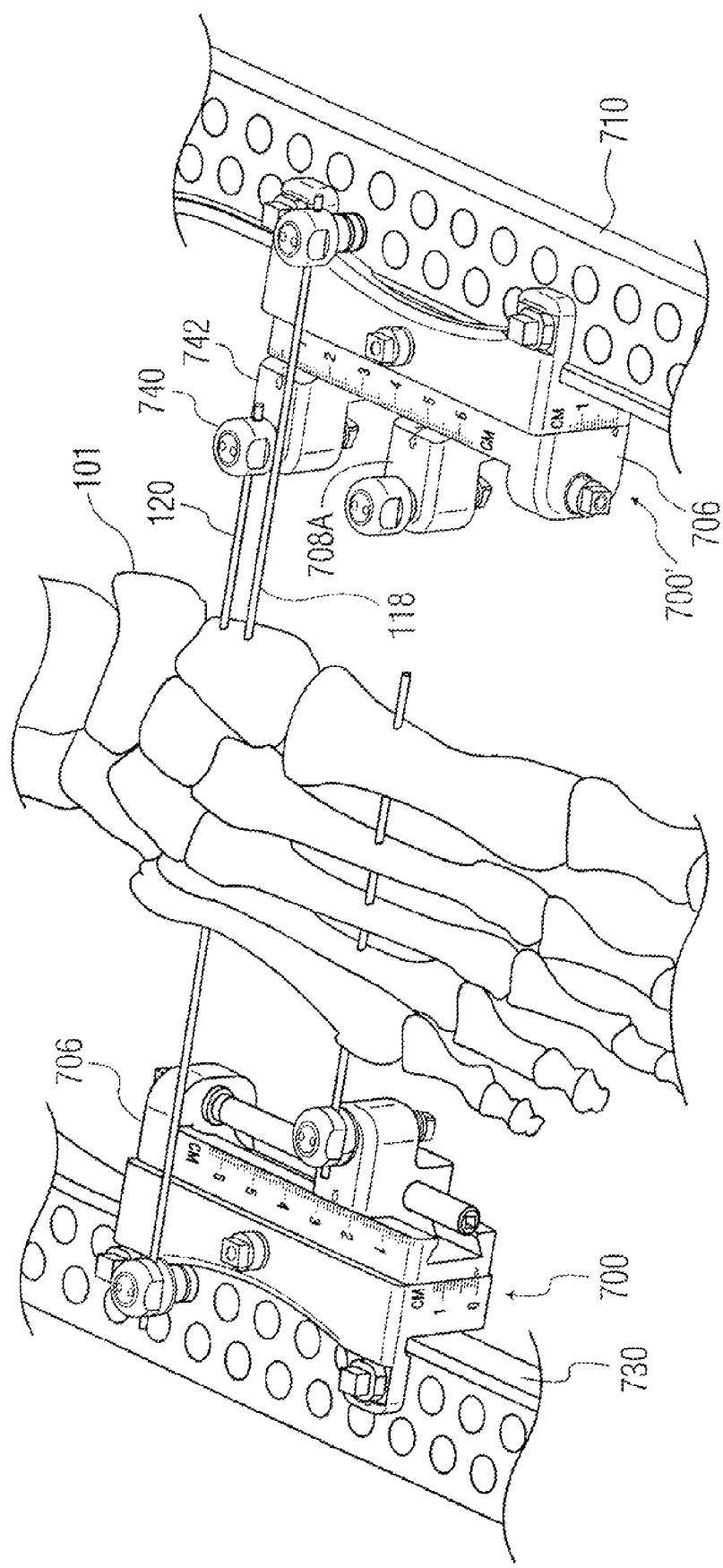
FIG. 11 is an enlarged isometric view of the ring and adjustable members of FIG. 10.

Referring to FIGS. 10 and 11, there is shown a top view of an alternate system in which the adjustable device 700 is mounted on the inner surface 730 of ring 704. Again, Kirschner wires 118 and 120 may be engaged with a foot 101.

Figure 12:
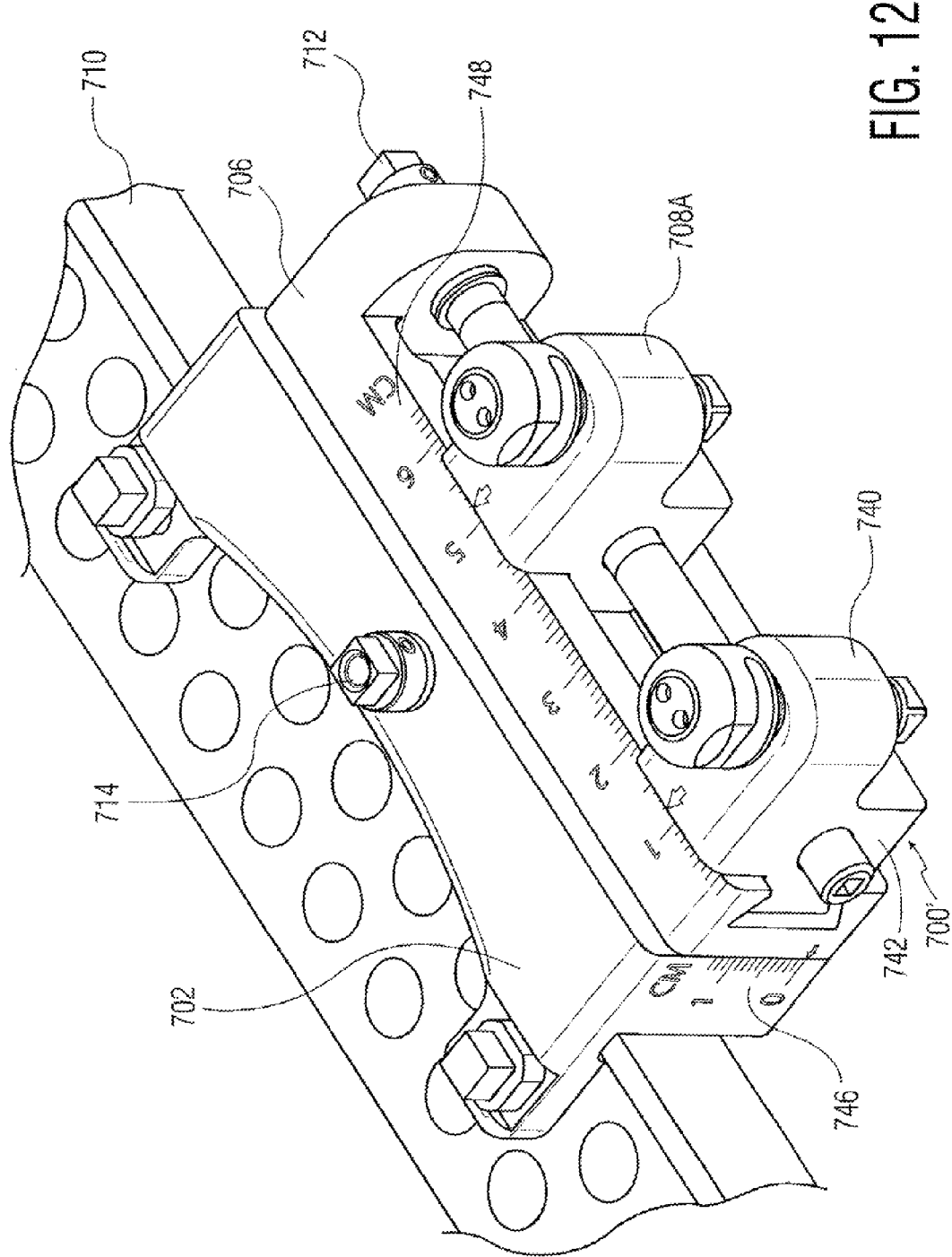
FIG. 12 is a top isometric view of an alternate adjustable device exhibiting two degrees of freedom.
Figure 13:
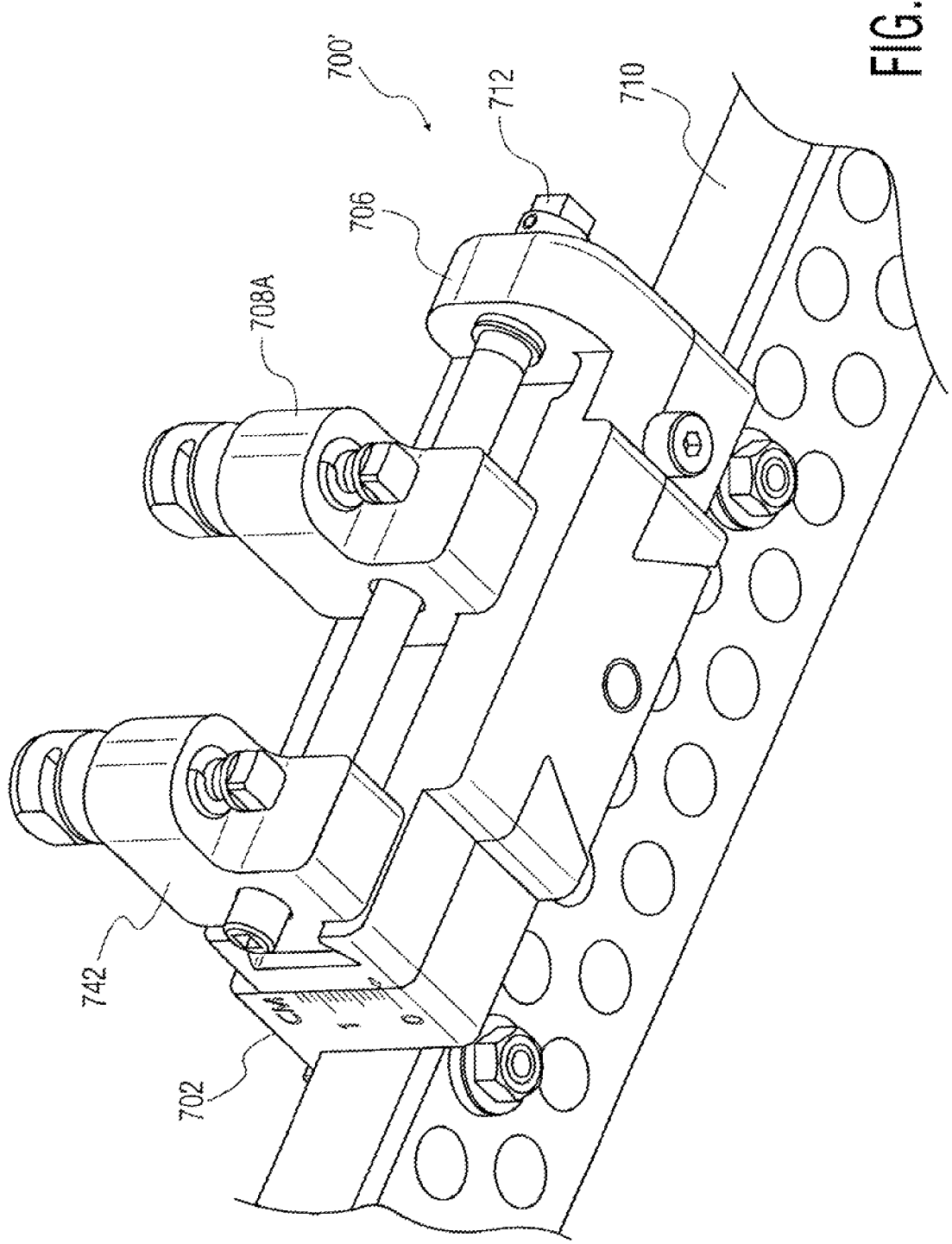
FIG. 13 is a bottom isometric view of the adjustable member of FIG. 12.

Referring to FIGS. 10 though 13, there is shown as an alternate adjustable device 700' which is similar to adjustable device 700 with the exception that a second pin holder 740 is attached to a block 742 which is slidably mounted within the groove 716 of element 706. Block 742 has a threaded bore which is mounted on screw shaft 712 and is moveable with respect to element 706. First block 708A is also provided with a pin holder and is operated as block 708. This allows the mounting of two Kirschner wires on element 706 with both Kirschner wires being adjustable along the length of the arm 710. Again, screw shaft 714 allows the block 706 to move in the direction perpendicular to the plane of arm 710. As shown in FIG. 12, indicators scales 746 and 748 may be provided to indicate the amount of movement of the Kirschner wires in millimeters.

Figure 14:
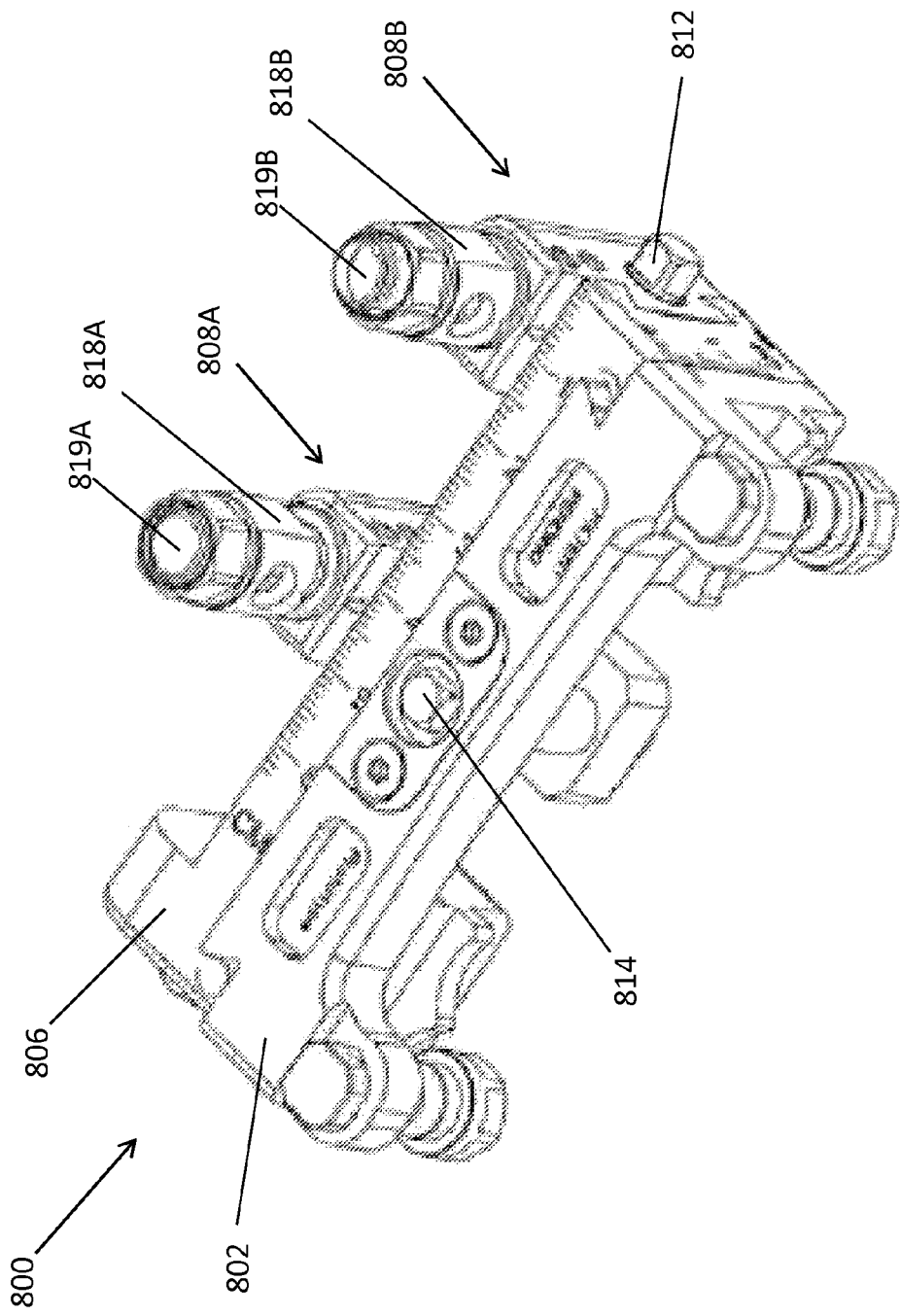
FIG. 14 is a perspective view of another alternate adjustable device.
Figure 17:
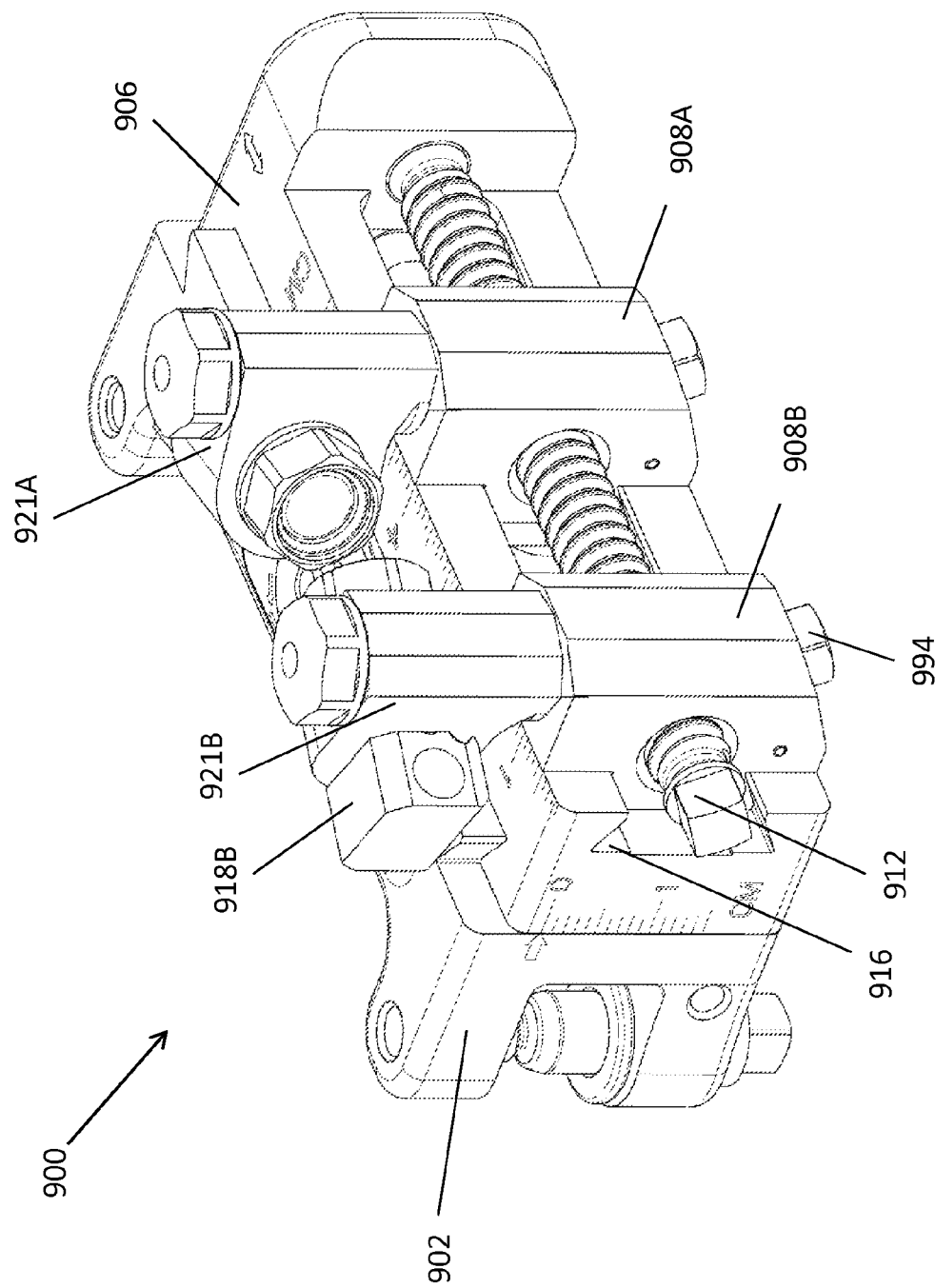
FIG. 17 is a top rear perspective view of a further alternate adjustable device.

Referring to FIGS. 14-16, there are shown multiple views of another alternate adjustable device 800 which is similar to adjustable device 700'. The device generally denoted as 800 includes a body 802, first member 806 and second members 808A and 808B. First and second members 808A and 808B each include a dovetail 828B extending from first and second members 808A and 808B that is slidably mounted in a groove 816 in member 806. The device 800 provides rotational movement between member 806 and 808A and 808B, but in different manner than first member 110 and second member 112 of device 100 as shown in FIG. 5, for example. This rotation is described in further detail below. Movement parallel to the ring is accomplished by rotating actuation member 812 (i.e. head of threaded rod) either clockwise or counterclockwise to translate elements 808A and 808B, while movement perpendicular to the ring is accomplished by rotating actuation member 814 (i.e. head of a threaded rod) either clockwise or counterclockwise to translate element 806 in relation to body 802. Pin holders 818A and 818B are operatively coupled to elements 808A and 808B, respectively.

Pins (or K-wires, or other fasteners) may be secured within apertures 815 of pin holders 818A and 818B. Each pin holder 818A and 818B may be rotated about an axis parallel to the axis of the tibia. The rotation may be effectuated, for example, by coupling a tool (not shown) to a nut 819A or 819B and rotating the nut. The rotation of the nut 819A or 819B causes the respective pin holder 818A or 818B to rotate as well. The elements 808A and 808B, to which the pin holders 818A and 818B are connected, do not rotate by virtue of their connection to screw shaft 812 and first member 806.

FIGS. 17-20 illustrate various views of yet a further embodiment of an adjustable device 900. Adjustable device 900 is similar to adjustable device 800, and provides for an additional degree of rotation. The device generally denoted as 900 includes a body 902, and first member 906 and second members 908A and 908B. First and second members 908A and 908B are slidably mounted in a groove 916 in member 906 via dovetails extending from the respective sliding element. The device 900 provides for two degrees of rotational movement between member 906 and 908A and 908B. This rotation is described in further detail below. Movement parallel to the ring is accomplished by turning screw shaft 912 to move elements 908A and 908B, while movement perpendicular to the ring is accomplished by turning screw shaft 914 and moving element 906 in relation to body 902. Pin holders 918A and 918B are rotatably coupled to vertical connectors 921A and 921B respectively.

Figure 18:
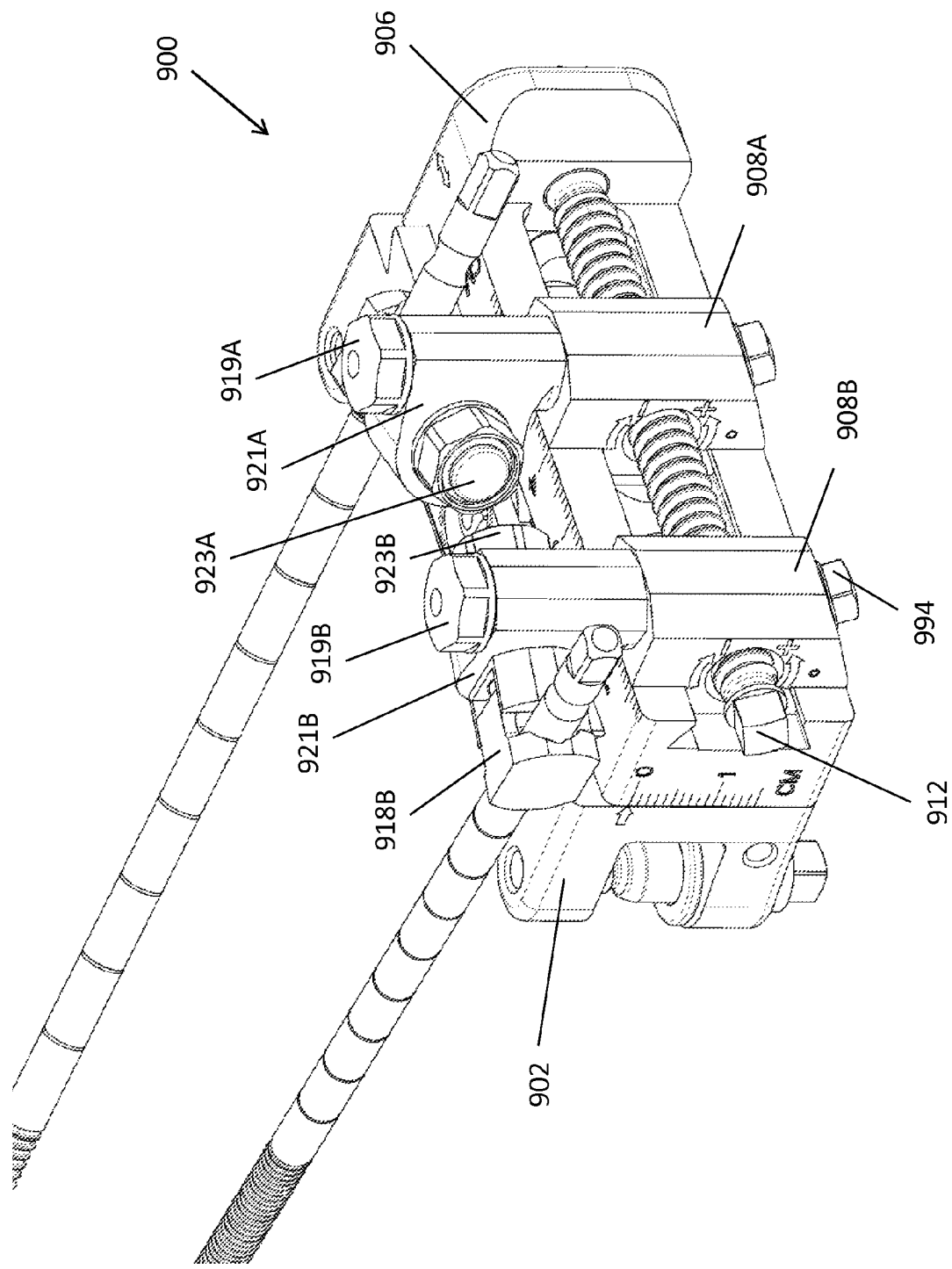
FIG. 18 is a rear perspective view of the device of FIG. 17 mated with bone fixation elements.
Figure 19:
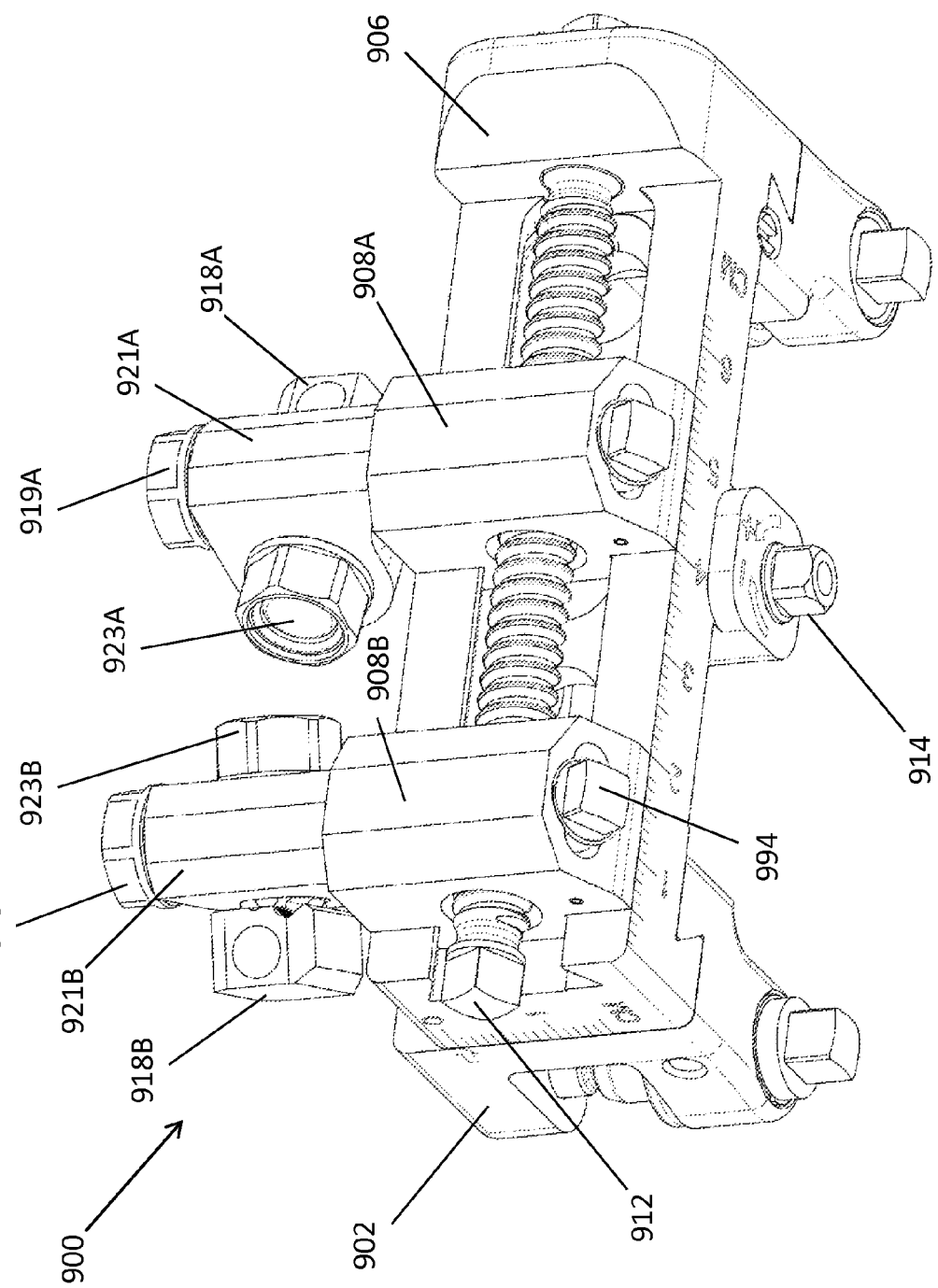
FIG. 19 is a bottom rear perspective view of the device of FIG. 17.

Pins (or K-wires, or other fasteners) may be secured within apertures of pin holders 918A and 918B, as illustrated in FIG. 18. Each pin holder 918A and 918B may be rotated about an axis parallel to the ring. The rotation may be effectuated, for example, by coupling a tool (not shown) to a nut 923A or 923B and rotating the nut. The rotation of the nut 923A or 923B causes the respective pin holder 918A or 918B to rotate as well. Further, vertical connectors 921A and 921B may each be rotated about an axis parallel to the tibia. The rotation of the nut 919A or 919B may similarly be effectuated by a tool (not shown). The elements 908A and 908B, to which the pin holders 918A and 918B and vertical connectors 921A and 921B are connected, do not rotate by virtue of their connection to screw shaft 912 and first member 906.

FIGS. 21A and 21B illustrate cross sectional views of second member 908B in a locked position and an unlocked position, respectively. A locking mechanism generally includes a rotatable nut 994, a compression pad 993, and a locking ball 992. The nut 994 is threadingly mated with an aperture in the second member 908B. As a user rotates the nut 994, the nut threads into the aperture until the compression pad 993 pushes the locking ball 992 into frictional engagement with the screw shaft 912. With enough force applied, the compression fit resists free sliding motion of the second member 908B along the screw shaft 912.

When in the locked position, as illustrated in FIG. 21A, the second member 908B can be translated along the screw shaft 912 by rotation of the screw shaft, as described above. When in the unlocked position, as illustrated in FIG. 21B, the second element 908B can be freely translated along the screw shaft 912 without rotating the screw shaft. As the second element 908B is freely translated along the screw shaft 912, a spring 991 and ball 990 are also translated along the screw shaft 912. The spring 991 biases the ball 990 toward the screw shaft 912. As the second element 908B is freely translated, the ball 990 helps locate the grooves of the threaded screw shaft 912 due to the force provided by the spring 991. Each time the ball 990 is pushed by the spring into a groove of the threading of screw shaft 912, an audible and/or tactile clicking may be produced to provide feedback that the ball 990 is within a groove of the threading of the screw shaft 912.

The locking mechanism may also include a fitting in the form of a ball 995. The ball 995 may fit into a corresponding groove in the aperture of the second element 908B. The ball 995 may also be located between two flanges on the nut 994 and sized such that, even upon continued rotation of the nut 994 in the unlocking direction, the nut resists complete disengagement from the aperture of the second member 908B. Similar or identical mechanisms to those described with relation to second member 908B can be provided for second member 908A for the same purposes. When in the unlocked position, second members 908A and 908B can be freely translated along the screw shaft 912 independently of each other. When each is locked, however, rotation of the screw thread 912 translates the second members 908A and 908B in unison.

Referring to FIG. 22, a side sectional view of the device 900 is illustrated. The device 900 includes a clamping mechanism that allows for connection of the device to rings of various thicknesses. More specifically, the body 902 includes a pair of connector systems 1002 (only one connector system visible in FIG. 22). The connector system 1002 generally includes a connector 1004 with a head 1006 and a threaded portion 1008. The threaded portion 1008 and part of the connector 1004 pass through a hole in a fixation ring, and the threaded portion threadingly engages an aperture 903 in the body 902 to secure the fixation ring relative to the body 902. The connector system 1002 also includes a nut 1010 which is threadedly secured to a clamp 1014, the nut 1010 and clamp 1014 acting as a single body. The nut 1010 is flush on the collar 1012 of head 1006.

The connector system 1002 may initially be in an open position that provides enough clearance for a fixation ring to be inserted into the body 902 (this position not illustrated). Once inserted into the body 902, a hole in the fixation ring is aligned with the connector system and the threaded portion 1008 of the connector 1004 is advanced through a hole in the fixation ring. This may initially be accomplished by pushing the head 1006 of the connector 1004 upwards until the threaded portion 1008 is adjacent to the threaded aperture 903 in the body 902. At that point, the head 1006 is rotated as the threads of the threaded portion 1008 engage the threaded aperture 903. As rotation continues, the nut 1010 is pushed upward, which in turn causes the clamp 1014 to be pushed upward. A top flange of the clamp 1014 advances with the connector 1004 until it contacts a face of the fixation ring. The flange of the clamp 1014 provides a surface on which a bottom face of a fixation ring rests, and thus allows for rings of various thicknesses to be securely supported by the body 902 in conjunction with the connector system 1002. Additional clamps, such as second clamp 1016, may also be used to allow for secured fixation of thinner fixation rings.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, elements described in relation to one embodiment may be used in combination with elements described in relation to another embodiment without departing from the scope of the invention.

The invention claimed is:

1. An external fixation system including a ring element and an adjustable bone fastener retaining device mounted on the ring element, the adjustable retaining device comprising:
    a body member releasably coupled to the ring element;
    a first member directly coupled to the body member and capable of translating with respect to the body member in a direction perpendicular to a planar surface of the ring element by actuation of a first drive screw;
    a second member directly coupled to the first member and capable of translating with respect to the first member in a direction parallel to a side wall of the ring element by actuation of a second drive screw; and
    a rotatable pin holder directly coupled to the second member and configured to receive therethrough at least a portion of a first bone fastener.

2. The external fixation system of claim 1, wherein the rotatable pin holder of the second member is configured to rotate about an axis perpendicular to the planar surface of the ring element.

3. The external fixation system of claim 2, further comprising:
    a third member coupled to the first member and capable of translating with respect to the first member in a direction parallel to a side wall of the ring element by actuation of the second drive screw,
    wherein the third member further includes a rotatable pin holder configured to receive therethrough at least a portion of a second bone fastener.

4. The external fixation system of claim 3, wherein the rotatable pin holder of the third member is configured to rotate about an axis perpendicular to the planar surface of the ring element.

5. The external fixation system of claim 3, wherein the first drive screw is mounted on the body member and is in engagement with a mating drive element on the first member, and the second drive screw is mounted on the first member and in threaded bores in the second and third members.

6. The external fixation system of claim 1, wherein the translation of the second member with respect to the first member is guided by a protrusion extending outwardly from the second member mated with a recess in the first member.

7. The external fixation system of claim 1, further comprising a rotatable connector coupled to the second member and adapted to rotatably mate with the rotatable pin holder.

8. The external fixation system of claim 7, wherein the rotatable connector is configured to rotate about an axis perpendicular to the planar surface of the ring element.

9. The external fixation system of claim 8, wherein the rotatable pin holder is configured to rotate about an axis perpendicular to the axis about which the rotatable connector is configured to rotate.

10. The external fixation system of claim 1, the second member further comprising:
    a locking mechanism including an actuation member and a locking member,
    wherein the locking mechanism is configured to change from an unlocked position to a locked position by actuating the actuation member, and
    wherein actuation of the actuation member drives the locking member into frictional engagement with the second drive screw.

11. The external fixation system of claim 10, wherein the locking member is a ball configured to fit between adjacent threads in the second drive screw.

12. The external fixation system of claim 10, wherein the second member, when the locking mechanism is in the unlocked position, is capable of linear motion with respect to the first member and the side wall of the ring element between first and second ends of the body without rotation of the second drive screw.

13. The external fixation system of claim 12, the second member further comprising;
    a locating ball; and
    a spring biasing the locating ball toward the second screw drive.

14. The external fixation system of claim 13, wherein the locating ball, while the second member is linearly moving with respect to the first member when the locking mechanism is in the unlocked position, consecutively enters grooves between adjacent screw threads in the second drive screw due to force provided by the spring.

15. The external fixation system of claim 14, wherein the locating ball provides at least one of auditory or tactile feedback upon entering a groove between adjacent screw threads in the second screw drive.

16. The external fixation system of claim 1, wherein the body further comprises a first flange and a second flange defining a gap space, the gap space configured to receive a portion of the ring element.

17. The external fixation system of claim 16, further comprising a connector system including a connector, a head at one end of the connector, and a threaded portion at a second end of the connector, the connector configured to extend through a hole in the portion of the ring element received in the gap space, and the threaded portion configured to threadingly engage an aperture in the first flange.

18. The external fixation system of claim 17, wherein the connector system further comprises a nut and a clamp, the nut and the clamp each surrounding portions of the connector.

19. The external fixation system of claim 18, wherein rotation of the head advances the threaded portion of the connector through the aperture in the first flange and further advances a flanged end of the clamp into engagement with the planar surface of the ring element.

20. A method for realigning, compressing, or distracting broken bones, comprising:
   providing an external fixation device having a ring member;
   fixing an adjustable device having a body to the ring member, the adjustable device having a first member directly and movably attached to the body, a second member directly and movably attached to the first member, a connector directly and rotatably attached to the second member, and a pin holder directly and rotatably attached to the connector;
   inserting a first pin member through a first piece of bone and affixing the first pin member to the ring member;
   inserting a second pin member through a second piece of bone and affixing the second pin member to the pin holder of the adjustable device; and
   adjusting a position of at least one of the first and second members of the adjustable device with respect to the body by rotating two drive screws in engagement with two mating drive elements formed in each of the first and second members to realign, compress, or distract the broken bones.

21. The method of claim 20, wherein the first and second members are adjusted by moving the first member in a direction perpendicular to a plane of the ring member.

22. The method of claim 21, wherein the second member is adjusted by linearly moving the second member with respect to the first member.

* * * * *

UNITED STATES PATENT AND TRADEMARK OFFICE
CERTIFICATE OF CORRECTION

Page 1 of 1

PATENT NO. : 8,906,020 B2
APPLICATION NO. : 13/788466
DATED : December 9, 2014
INVENTOR(S) : Crozet et al.

It is certified that error appears in the above-identified patent and that said Letters Patent is hereby corrected as shown below:

\*\*On the title page, item (72) "Wakia" should read --Walla--

In the Specification
Column 7, line 24, "Protrusions" should read --Protrusion--
Column 7, line 67, "depicts" should read --depicting--
Column 9, line 3, "Pin holder" should read --A pin holder--
Column 9, line 11, "includes" should read --include--
Column 9, line 20, delete "as"
Column 9, line 32, "indicators" should read --indicator--.\*\*

Signed and Sealed this
Twenty-first Day of April, 2015

Michelle K. Lee
*Director of the United States Patent and Trademark Office*

UNITED STATES PATENT AND TRADEMARK OFFICE
CERTIFICATE OF CORRECTION

PATENT NO.        : 8,906,020 B2  
APPLICATION NO.   : 13/788466  
DATED             : December 9, 2014  
INVENTOR(S)       : Crozet et al.

Page 1 of 1

It is certified that error appears in the above-identified patent and that said Letters Patent is hereby corrected as shown below:

\*\*On the title page, item (72) "Walla" should correctly read --Walia--

In the Specification  
Column 7, line 24, "Protrusions" should read --Protrusion--  
Column 7, line 67, "'depicts" should read --depicting--  
Column 9, line 3, "Pin holder" should read --A pin holder--  
Column 9, line 11, "includes" should read --include--  
Column 9, line 20, delete "as"  
Column 9, line 32, "indicators" should read --indicator--\*\*

This certificate supersedes the Certificate of Correction issued April 21, 2015.

Signed and Sealed this  
Sixteenth Day of June, 2015

Michelle K. Lee  
*Director of the United States Patent and Trademark Office*